(12) United States Patent
Osypka et al.

(10) Patent No.: US 10,470,718 B2
(45) Date of Patent: Nov. 12, 2019

(54) METHOD FOR DIGITAL DEMODULATION AND FURTHER PROCESSING OF SIGNALS OBTAINED IN THE MEASUREMENT OF ELECTRICAL BIOIMPEDANCE OR BIOADMITTANCE IN A HUMAN SUBJECT

(71) Applicant: Osypka Medical GmbH, Berlin (DE)

(72) Inventors: Markus J. Osypka, La Jolla, CA (US); Eberhard Gersing, Goettingen (DE)

(73) Assignee: OSYPKA MEDICAL GMBH, Berlin (DE)

( * ) Notice: Subject to any disclaimer, the term of this patent is extended or adjusted under 35 U.S.C. 154(b) by 1632 days.

(21) Appl. No.: 14/091,032

(22) Filed: Nov. 26, 2013

(65) Prior Publication Data

US 2014/0088902 A1 Mar. 27, 2014

Related U.S. Application Data

(62) Division of application No. 11/506,369, filed on Aug. 17, 2006, now abandoned.

(30) Foreign Application Priority Data

Aug. 17, 2005 (EP) .................................. 05017871

(51) Int. Cl.
*A61B 5/00* (2006.01)
*A61B 5/053* (2006.01)
*A61B 5/08* (2006.01)

(52) U.S. Cl.
CPC .......... *A61B 5/7239* (2013.01); *A61B 5/7228* (2013.01)

(58) Field of Classification Search
CPC ... A61B 5/7225; A61B 5/7228; A61B 5/7271; A61B 5/7278; A61B 5/053;

(Continued)

(56) References Cited

U.S. PATENT DOCUMENTS 1,908,688 A 5/1933 Call
2,327,874 A 8/1943 De Jong
(Continued)

FOREIGN PATENT DOCUMENTS

DE 199 14 437 10/2000
EP 0 480 078 4/1992
(Continued)

OTHER PUBLICATIONS

Bleicher, W et al; "Automatic Device for Noninvasive Monitoring of Stroke Volume, Cardiac Output, Systolic Time Intervals, and Derived Hemodynamic Parameters"; Computers in Cardiology; pp. 419-422; Oct. 22, 1980.

(Continued)

*Primary Examiner* — Adam J Eiseman
(74) *Attorney, Agent, or Firm* — Martin & Ferraro, LLP

(57) ABSTRACT

Methods and apparatus for digital demodulation of signals obtained in the measurement of electrical bioimpedance or bioadmittance of an object. One example comprises: generating an excitation signal of known frequency content; applying the excitation signal to the object; sensing a response signal of the object; sampling and digitizing the response signal to acquire a digitized response signal representing the response signal with respect to frequency content, amplitude and phase; correlating, for each frequency $f_{AC}$ of the excitation signal applied, digitized samples of the response signal, with discrete values representing the excitation signal; calculating, using the correlated signals for each frequency $f_{AC}$ of the excitation signal applied, complex values for the bioimpedance $Z(f_{AC})$; providing, over time, a set of digital bioimpedance waveforms $Z(f_{AC},t)$; separating the base bioimpedance $Z_0(f_{AC})$, from the waveforms; and separating the changes of bioimpedance $\Delta Z(f_{AC},t)$, from the waveforms.

6 Claims, 14 Drawing Sheets

(58) Field of Classification Search
CPC ... A61B 5/0535; A61B 5/0537; A61B 5/0809; A61B 5/7239
USPC .......................... 600/506, 529, 536, 547, 548
See application file for complete search history.

(56) References Cited

U.S. PATENT DOCUMENTS

| | | |
|---|---|---|
| 3,284,724 A | 11/1966 | Marlow |
| 3,340,867 A | 9/1967 | Kubicek et al. |
| 3,402,572 A | 9/1968 | Chase et al. |
| 3,601,126 A | 8/1971 | Estes |
| 3,971,365 A | 7/1976 | Smith |
| 4,001,554 A | 1/1977 | Hall et al. |
| 4,057,736 A | 11/1977 | Jeppson |
| 4,168,459 A | 9/1979 | Roesel, Jr. |
| 4,207,772 A | 6/1980 | Stoller |
| RE30,750 E | 9/1981 | Diack et al. |
| 4,289,142 A | 9/1981 | Kearns |
| 4,354,501 A | 10/1982 | Colley et al. |
| 4,387,722 A | 6/1983 | Kearns |
| 4,416,277 A | 11/1983 | Newton et al. |
| 4,450,527 A | 5/1984 | Sramek |
| 4,504,882 A | 3/1985 | Breton |
| 4,509,526 A | 4/1985 | Barnes et al. |
| 4,562,843 A | 1/1986 | Djordjevich et al. |
| 4,807,638 A | 2/1989 | Sramek |
| 4,836,214 A | 6/1989 | Sramek |
| 4,850,361 A | 7/1989 | Maekawa |
| 4,858,614 A | 8/1989 | Stevens et al. |
| 4,953,556 A | 9/1990 | Evans |
| 5,052,395 A | 10/1991 | Burton et al. |
| 5,103,828 A | 4/1992 | Sramek |
| 5,178,151 A | 1/1993 | Sackner |
| 5,178,154 A | 1/1993 | Ackmann et al. |
| 5,188,106 A | 2/1993 | Nappholz et al. |
| 5,241,964 A | 9/1993 | McQuilkin |
| 5,280,429 A | 1/1994 | Withers |
| 5,309,917 A | 5/1994 | Wang et al. |
| 5,311,878 A | 5/1994 | Brown et al. |
| 5,316,004 A | 5/1994 | Chesney et al. |
| 5,423,326 A | 6/1995 | Wang et al. |
| 5,443,073 A | 8/1995 | Wang et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,642,734 A | 7/1997 | Ruben et al. |
| 5,685,316 A | 11/1997 | Schookin et al. |
| 5,782,774 A | 7/1998 | Shmulewitz |
| 5,791,349 A | 8/1998 | Shmulewitz |
| 6,016,445 A | 1/2000 | Baura |
| 6,058,325 A | 5/2000 | Baura |
| 6,095,987 A | 8/2000 | Shmulewitz et al. |
| 6,102,869 A | 8/2000 | Meier et al. |
| 6,161,038 A | 12/2000 | Schookin et al. |
| 6,169,914 B1 | 1/2001 | Hovland et al. |
| 6,186,955 B1 | 2/2001 | Baura |
| 6,198,972 B1 | 3/2001 | Hartlaub et al. |
| 6,238,349 B1 | 5/2001 | Hickey |
| 6,263,243 B1 | 7/2001 | Lang |
| 6,275,012 B1 | 8/2001 | Jabaji |
| 6,292,377 B1 | 9/2001 | Sasaki |
| 6,316,518 B1 | 11/2001 | Phipps et al. |
| 6,334,849 B1 | 1/2002 | Sunagawa |
| 6,336,045 B1 | 1/2002 | Brooks |
| 6,404,089 B1 | 6/2002 | Tomion |
| 6,442,422 B1 | 8/2002 | Duckert |
| 6,490,474 B1 | 12/2002 | Willis et al. |
| 6,494,832 B1 | 12/2002 | Feldman et al. |
| 6,511,438 B2 | 1/2003 | Bernstein et al. |
| 6,633,777 B2 | 10/2003 | Szopinski |
| 6,641,520 B2 | 11/2003 | Bailey et al. |
| 7,186,219 B2 | 3/2007 | Osypka et al. |
| 7,822,470 B2 | 10/2010 | Osypka et al. |
| 7,904,141 B2 | 3/2011 | Osypka et al. |
| 2002/0193689 A1 | 12/2002 | Bernstein et al. |
| 2003/0052564 A1 | 3/2003 | Wilsdorf |
| 2003/0206021 A1 | 11/2003 | Laletin et al. |
| 2004/0143297 A1 | 7/2004 | Ramsey |
| 2004/0152996 A1 | 8/2004 | Gersing |
| 2004/0158167 A1 | 8/2004 | Smith et al. |
| 2005/0012414 A1 | 1/2005 | Gersing |
| 2007/0043303 A1 | 2/2007 | Osypka et al. |
| 2011/0190601 A1 | 8/2011 | Osypka et al. |

FOREIGN PATENT DOCUMENTS

| | | |
|---|---|---|
| EP | 1 754 441 B1 | 1/2008 |
| GB | 618405 | 2/1949 |
| WO | WO 02/094090 | 11/2002 |
| WO | WO 2004/047635 A1 | 6/2004 |

OTHER PUBLICATIONS

European Patent Office, European search report, Application No. EP 05017871, dated Nov. 2, 2005, 4 pages.

Lababidi, Z., et al; "The First Derivative Thoracic Impedance Cardiogram"; Circulation; vol. XLI: cover page and pp. 651-658; Apr. 1970.

Spitaels, S., et al.; "The Influence of Heart Rate and Age on the Systolic and Diastolic Time Intervals in Children"; Circulation; vol. XLIX: cover page and pp. 1107-1115; Jun. 1974.

Wallace, Arthur W.; "Endotracheal Cardiac Output Monitor"; Anesthesiology; vol. 92: 178-89; Jan. 2000.

Weissler, A., et al; "Systolic Time Intervals in Heart Failure in Man"; Circulation; vol. XXXVII: cover page and pp. 149-159; Feb. 1968.

With Use of Calibration Impedance | Without Use of Calibration Impedance

Fig. 4

Apply CAL, OBJ Impedances
(Indirect Correlation):

Measure CAL Current
Measure CAL Voltage
Measure OBJ Current
Measure OBJ Voltage
Option: Fit measured signals Correlate CAL Current samples & SIN, COS samples
Correlate CAL Voltage samples & SIN, COS samples
Correlate OBJ Current samples & SIN, COS samples
Correlate OBJ Voltage samples & SIN, COS samples

Fig. 7

Apply OBJ Impedance only
(Indirect Correlation):

Measure OBJ Current
Measure OBJ Voltage
Option: Fit measured signals

Correlate OBJ Current samples & SIN, COS samples
Correlate OBJ Voltage samples & SIN, COS samples

Fig. 5

Apply CAL, OBJ Impedances
(Direct Correlation):

Measure CAL Current
Measure CAL Voltage
Measure OBJ Current
Measure OBJ Voltage
Option: Fit measured signals Correlate CAL Voltage samples & CAL Current samples
Correlate OBJ Voltage samples & OBJ Current samples

Fig. 8

Apply OBJ Impedance only
(Direct Correlation):

Measure OBJ Current
Measure OBJ Voltage
Option: Fit measured signals

Correlate OBJ Voltage samples & OBJ Current samples

With Current Measurement
---
Without Current Measurement

Fig. 6

Apply CAL, OBJ Impedances:

Measure CAL Voltage
Measure OBJ Voltage
Option: Fit measured signals

Correlate CAL Voltage samples & SIN, COS samples
Correlate OBJ Voltage samples & SIN, COS samples

Fig. 9

Apply OBJ Impedance only:

Measure OBJ Voltage
Option: Fit measured signals

Correlate OBJ Voltage samples & REF Current samples

Fig. 3

METHOD FOR DIGITAL DEMODULATION AND FURTHER PROCESSING OF SIGNALS OBTAINED IN THE MEASUREMENT OF ELECTRICAL BIOIMPEDANCE OR BIOADMITTANCE IN A HUMAN SUBJECT

CROSS-REFERENCE TO RELATED APPLICATIONS

This is a divisional of U.S. application Ser. No. 11/506,369, filed Aug. 17, 2006, which claims priority to European Patent Application No. EP05017871, filed Aug. 17, 2005, titled "Method and apparatus for digital demodulation and further processing of signals obtained in the measurement of electrical bioimpedance or bioadmittance in an object", which is incorporated herein by this reference.

BACKGROUND

1. Technical Field

This invention is related to the field of digital demodulation and further processing of signals obtained from the measurement of electrical bioimpedance or bioadmittance in a biological object, for instance an animal or a human due to cardiac and/or respiratory activity, for instance in cardiometry, in particular to the monitoring through measurement of the change in thoracic electrical bioimpedance (TEB) or bioadmittance, and pertains to the processing of the excitation, response and/or reference signals obtained through sensing and measuring excitation, response and/or reference signals, e.g., but not limited to, a voltage resulting from an alternating current (AC) application.

2. Description of Related Art

Background of the Invention

Noninvasive hemodynamic monitoring utilizes the measurement of thoracic electrical bioimpedance (TEB) for the determination of stroke volume, cardiac output and other cardiopulmonary parameters in humans or animals.

For this purpose, an alternating current of known (e.g., constant amplitude) is applied to current electrodes, e.g. surface electrodes, located e.g. at one or both sides of the neck and the lower thorax, approximately at the level of the xiphoid process (Sramek B.: U.S. Pat. No. 4,450,527; Osypka M. J., Bernstein D. P.: Electrophysiological Principles and Theory of Stroke Volume Determination by Thoracic Electrical Bioimpedance. AACN Clinical Issues 1999; 10, 3: 385-399). The resulting voltage is sensed through sensing electrodes, e.g. other surface spot electrodes, and measured.

Alternatively, current electrodes (surface electrodes) are applied to the forehead, or substituted by band electrodes around the circumferences of the neck and the lower thorax (Kubicek W. G.: U.S. Pat. No. 3,340,867) or by current electrodes located on an esophageal catheter (Sramek B.: U.S. Pat. No. 4,836,214) or an implantable pacemaker or defibrillator lead, with the latter applications focusing on the heart rather than the overall thorax.

The voltage resulting from constant alternating current application, which is proportional to the thoracic electrical impedance, is modulated onto an alternating voltage signal of the frequency of the alternating current (AC) applied.

A common approach in the acquisition of the thoracic impedance applies an active high-pass or band-pass filter to the voltage signal obtained from the sensing electrodes. Each individual signal is further demodulated through a diode rectifier circuit, and fed into the input of a differential amplifier. The differential signal which is proportional to $Z(t)$ in the event of a constant alternating current (AC) application, is then separated, in the analog domain, into a DC voltage proportional to the base impedance $Z_0$ and the change in impedance $\Delta Z(t)$. Both analog signals $Z_0$ and $\Delta Z(t)$ are then digitized for further processing.

However, conventional demodulation by diodes and subsequent low-pass filtering exhibit certain drawbacks. Diode characteristics change with temperature. Moreover, even a full-wave rectified sinusoidal signal is difficult to smooth; the time constant of the smoothing low-pass filter cannot be chosen appropriately high because the bandwidth of the desired demodulated signal will be limited, and critical waveform detail can be lost. Digitization of a signal with ripple can produce unstable data, due to the fact that the values of the samples of the demodulated signal depend on the position of the sampling within the period of the carrier signal.

In order to improve accuracy and stability and to ease adaptation to changing conditions, Osypka et al. developed a technique using a phase sensitive detector, a subsequent integrator and a high resolution analog-to-digital converter (ADC), followed by digital signal processing (DSP) (Osypka M. J. and Schafer E. E., Impedance Cardiography: Advancements in System Design. In: Riu P J, Rosell J, Bragós R, Casas O (eds.): Proceedings of the X. International Conference on Electrical Bio-Impedance (ICEBI), Barcelona, Spain, Apr. 5-9, 1998). The demodulation is, however, achieved with analog circuitry. The voltage obtained from the thorax is fed into a phase-sensitive detector (PSD) circuit. The reference trigger signal for the PSD is derived from the alternating sinusoidal current generator, followed by a phase shifter to adjust the reference phase for detecting the real (or imaginary) part of impedance, and a comparator switching at the zero-crossings of the applied sinusoidal current. The output of the PSD consists of the full wave rectified carrier signal containing the information on the real or imaginary part of the thoracic impedance, depending on the reference phase. The following stage provides the smoothing of the demodulated signal by integration over an integer number of cycles of the carrier frequency, which corresponds, for instance, to an integration time of 1 millisecond. Integration begins after the integration capacitor has been discharged by a reset signal, and ends prior to the start signal for the high-resolution ADC. The timing control is initialized by the reference trigger signal for the PSD, ensuring that the integration is performed over a number of complete periods of the carrier signal, and provides the appropriate start pulses for the ADC. By this process, the demodulated impedance signal $Z(t)$ is "updated" every millisecond. A high resolution ($\geq 20$ bit) ADC measures the charge accumulated during the integration, which is proportional to the thoracic impedance $Z(t)$. The integration period, i.e. the time constant of averaging, can be easily changed.

For the purpose of determining the change in thoracic electrical bioimpedance, the theoretical sound approach has significant practical limitations. First, circuit design will compromise on the theoretically available resolution of 20 bits. More realistic, a resolution of 14-16 bits is achievable. The second limitation is due to the thoracic bioimpedance signal itself: $Z(t)$ consists of a portion, which is quasi-constant over time and further referred to as $Z_0$, and another portion $\Delta Z(t)$, which changes during cardiac and respiration cycles:

$$Z(t)=Z_0+\Delta Z(t).$$

In particular the amplitudes of changes in bioimpedance due to the pump function of the heart are very small compared to $Z_0$. With a large offset ($Z_0$) taking up approximately 8 bits of resolution, the remaining 6-8 bits are available for quantization of the dynamic portion of $Z(t)$, namely $\Delta Z(t)$.

Problem Underlying the Invention

It is an object of the present invention to propose a method and an apparatus for digital demodulation and further processing of signals obtained in the single and multi-frequency ($f_{AC}$) measurement of electrical bioimpedance $$Z(f_{AC},t)=Z_0(f_{AC})+\Delta Z(f_{AC},t)$$

or electrical bioadmittance $$Y(f_{AC},t)=Y_0(f_{AC})+\Delta Y(f_{AC},t)$$

in a biological object in which the amplitude of changes or rate of changes in electrical bioimpedance, $\Delta Z(f_{AC},t)$, or bioadmittance, $\Delta Y(f_{AC},t)$, due to biological functions of the biological object, such as plants or as animals or humans, with the latter for instance due to respiratory or cardiac functions including the pump function of the heart, can be determined with a higher amplitude resolution than before.

SUMMARY

The method and apparatus according to the present invention as defined in the appended claims employs digital demodulation by means of correlation, also called correlation or matched filter technique, and further digital signal processing followed by a calculation of a complex value for the bioimpedance or bio admittance, respectively, for each frequency $f_{AC}$ of an excitation signal of known frequency content, preferably an alternating current (AC), applied, providing, over time, a set (spectrum) of bioimpedance waveforms, $Z(f_{AC},t)$, or bioadmittance waveforms, $Y(f_{AC},t)$, with $$Z(f_{AC},t)=Z_0(f_{AC})+\Delta Z(f_{AC},t)$$

$$Y(f_{AC},t)=Y_0(f_{AC})+\Delta Y(f_{AC},t)$$

to which a first filter, preferably a low pass filter, is applied to separate the base impedance, $Z_0(f_{AC})$, or the base admittance, $Y_0(f_{AC})$, therefrom, and a second filter, preferably a high pass filter, is applied to separate the change in the electrical bioimpedance over time, $\Delta Z(f_{AC},t)$, or the change in the electrical bioadmittance over time, $\Delta Y(f_{AC},t)$.

$\Delta Z(f_{AC},t)$ or directly $Z(f_{AC},t)$, or $\Delta Y(f_{AC},t)$ or directly $Y(f_{AC},t)$, can be input to a differentiator in order to obtain the rate of change of the changes in bioimpedance, $d(\Delta Z(f_{AC},t))/dt$, or the rate of change of the bioimpedance (waveforms), $dZ(f_{AC},t)/dt$, respectively, or the rate of change of the changes in bioadmittance $d(\Delta Y(f_{AC},t))/dt$ or the rate of change of the bioadmittance (waveforms), $dY(f_{AC},t)/dt$, respectively.

In the claims the term excitation signal as used is intended to encompass a voltage signal, a current signal and an electro-magnetic field signal for application to the object.

The term signal of known frequency content means that the signal is defined as regards to a single frequency or a composite frequency composed of a number of superimposed frequencies. In the embodiment in which the excitation signal is measured the amplitude and phase of the excitation signal must not be known a priori.

The term correlating includes several meanings: a) correlation of said digitized excitation signal with said digitized response signal; b) correlation of said digitized excitation signal delayed by 90° with said digitized response signal; c) correlation of said digitized excitation signal with the digital values of an ideal sinusoidal signal (sin, cos) (reference signal to the excitation signal), and d) correlation of said digitized response signal with the digital values of an ideal sinusoidal signal (sin, cos) (reference signal to the excitation signal).

Like conventional approaches for bioimpedance or bioadmittance measurements in cardiometry, the excitation signal is preferably an alternating current of known frequency or frequencies $f_{AC}$ with related amplitude(s) and phase(s), preferably of constant magnitude, and is applied to the object, e.g. a human thorax, or a portion of it, or arm, or limb, or heart, or trachea, or the esophagus via electrodes located on the skin surface, or tracheal or esophageal catheters or probes, or implantable pacemaker or defibrillator leads, Unlike conventional approaches, the response signal, i.e., the voltage resulting from the current application, which, in the event of an AC application with constant magnitude, is proportional to the bioimpedance or reciprocal to the bioadmittance, is sampled and digitized as early as possible, prior to any demodulation. The demodulation is accomplished by digital signal processing (DSP) directly or indirectly correlating the measured with digitized signal waveforms representing the response signal, particularly the voltage signal measured across the object, and the excitation signal, particularly the alternating current (AC) applied across the object, for example, the human or animal thorax, or a portion of it (direct correlation) or a reference signal to the excitation signal (indirect correlation).

With the sampling rate being significantly higher than the highest frequency component of the excitation signal, particularly an alternating current (AC), applied, the method and apparatus according to the invention provides measurement results at not only a sufficient resolution but a very high amplitude resolution. Unlike common approaches proposed for the display of multi-frequency bioimpedance (Withers P. O.: U.S. Pat. No. 5,280,429) and in a real-time electrical impedance tomography system (Brown B. H. and Barber D. C.: U.S. Pat. No. 5,311,878), bioimpedance or bioadmittance cardiometry requires a high resolution and accuracy of correlation results because the changes related to the cardiac cycle are significantly smaller in amplitude than the quasi-constant portion. If the influence of respiration or ventilation is suppressed, or the corresponding effect on the impedance respectively admittance signal is filtered out, only the cardiac-induced pulsatile impedance or admittance component remains. By magnitude, $\Delta Z(f_{AC},t)$ for instance is approximately 0.3% to 0.5% of $Z_0$ (Osypka M. J. and Bernstein D. P.: Electrophysiologic Principles and Theory of Stroke Volume Determination by Thoracic Electrical Bioimpedance; AACN Clinical Issues 1999: 10, 3: 385-399).

Furthermore, the method and apparatus according to the invention separate for one or more frequencies $f_{AC}$ of the excitation signal, e.g. the alternating current (AC) applied, the change in electrical bioimpedance, $\Delta Z(f_{AC},t)$, from the offset, or base impedance $Z_0$, or the change in electrical bioadmittance, $\Delta Y(f_{AC},t)$, from the offset, or base admittance $Y_0$, and determine $\Delta Z(f_{AC},t)$, or $\Delta Y(f_{AC},t)$, respectively, $\Delta Z(f_{AC},t)$ or directly $Z(f_{AC},t)$, or $\Delta Y(f_{AC},t)$ or directly $Y(f_{AC},t)$, as they are differentiated, e.g. by inputting to a differentiator in order to obtain the rate of change in bioimpedance, $dZ(f_{AC})/dt$, or the rate of change in bioadmittance, $dY(f_{AC})/dt$, respectively, with high resolution.

Unlike common approaches proposed for the display of multi-frequency bioimpedance (Withers P. O.: U.S. Pat. No. 5,280,429), where the complex Fourier transform of the complex cross-correlation signal (as a function of time delay between the excitation and response signals) is determined, the method and apparatus according to one embodiment of the invention perform the correlation separately for each frequency $f_{AC}$, of the excitation signal applied (in the description further referred to as indirect correlation), correlating digitized samples of the measured, sampled and digitized response signals with digital samples of ideal sinusoids being reference signals to the excitation signal.

The method and apparatus according to the invention propose embodiments with and without incorporation of a calibration impedance in connection with the suppression of the influence of electrical circuit properties and its influence on the measurement.

Furthermore, signal curve fitting is envisaged as an option for signals in noisy environments.

The method and apparatus determine, for one frequency, or several frequency components, of the excitation signal, particularly the alternating current applied, the complex bioimpedance, or complex bioadmittance, i.e. the real part (in-phase portion) and the imaginary part (quadrature portion) of the impedance, or admittance, at a high amplitude resolution, which is required to separate the change in electrical bioimpedance, $\Delta Z(f_{AC},t)$, from the offset, or base impedance, $Z_0(f_{AC})$, or the change in electrical bioadmittance, $\Delta Y(f_{AC},t)$, from the offset, or base admittance, $Y_0(f_{AC})$, and determine $\Delta Z(f_{AC},t)$, or $\Delta Y(f_{AC},t)$, respectively, and $dZ(f_{AC},t)$, or $dY(f_{AC},t)$ respectively, with high resolution.

Theoretically the correlation process is derived from the Fourier transform for periodical signals $s(t)$:

$$s(t) = \frac{a_0}{2} + \sum_{v=1}^{V}(a_v\cos(v\omega_0 t) + b_v\sin(v\omega_0 t))$$

where $$\frac{a_0}{2}$$

designates the offset,
$\omega_0$ is the basic frequency,
$v$ is the number of the harmonic of the base frequency $\omega_0$, and $$a_v = \frac{2}{N}\sum_{n=1}^{N} s_n\cos(v\omega_0 t_n),$$
$$v = 0, 1, \ldots, V$$

represents the quadrature portion, or imaginary part, of each frequency component of $s(t)$, and $$b_v = \frac{2}{N}\sum_{n=1}^{N} s_n\sin(v\omega_0 t_n),$$
$$v = 0, 1, \ldots, V$$

represents the in-phase portion, or real part, of each frequency component of $s(t)$.

$N$ represents the number of samples obtained at equidistant time intervals at points in time $t_n$ ($N>2V+1$). The samples of $s(t)$ are referred to as $s_n$.

Because the frequency of the alternating current (AC) applied is known a priori ($v=1$), the Fourier transform is reduced to $$s(t) = a_1\cos(\omega_0 t) + b_1\sin(\omega_0 t).$$

A band pass filter is applied to $s(t)$ for suppression of noise.

The application of digital demodulation has already been proposed for the multi-frequency measurement of impedances (Osypka M., Schmerbeck A., Gersing E., and Meyer-Waarden K.: Determination of electric impedances of tissue at a frequency range of 5 Hz to 20 kHz by digital correlation technique. In: Nikiforidis G., Pallikaridis N., Proimos B. (eds.): Proceedings V. Mediterranean Conference on Medical and Biological Engineering (MEDICON 89), Aug. 29-Sep. 1, 1989, University of Patras, Greece; Withers P. O.: U.S. Pat. No. 5,280,429) and for an electrical impedance tomography system (Osypka M., Gersing E., and Meyer-Waarden K.: Komplexe elektrische Impedanztomografie im Frequenzbereich von 10 Hz bis 50 kHz. Z. Med. Phys. 3 (1993), 124-132; Osypka M. and Gersing E.: Parallel signal processing and multi-electrode current feeding in a multi-frequency EIT system. Innovation et Technologie en Biologie et Medicine, Vol. 15, Special Issue 1, 1994, pp. 56-61; Brown B. H. and Barber D. C.: U.S. Pat. No. 5,311,878). Application for determination of the base impedance, $Z_0(f_{AC})$, the change in electrical bioimpedance $\Delta Z(f_{AC},t)$, and the rate of change in electrical bioimpedance, $dZ(f_{AC})/dt$ or the base admittance, $Y_0(f_{AC})$, the change in electrical bioadmittance $\Delta Y(f_{AC},t)$, or the rate of change in bioelectrical admittance $dY(f_{AC})/dt$, with high resolution was not considered.

BRIEF DESCRIPTION OF THE DRAWINGS

Preferred embodiments of the apparatus of the invention are described in the following with respect to the drawings. However, this description is of exemplary nature and does not limit the spirit and scope of the invention as defined in the claims and equivalents thereof.

FIG. 2b provides charts for a graphic description of the correlation method of FIG. 2a;

FIG. 3 is a systematic overview of the modes of measurement of the embodiments of FIG. 4-9;

DETAILED DESCRIPTION

Figure 1A:
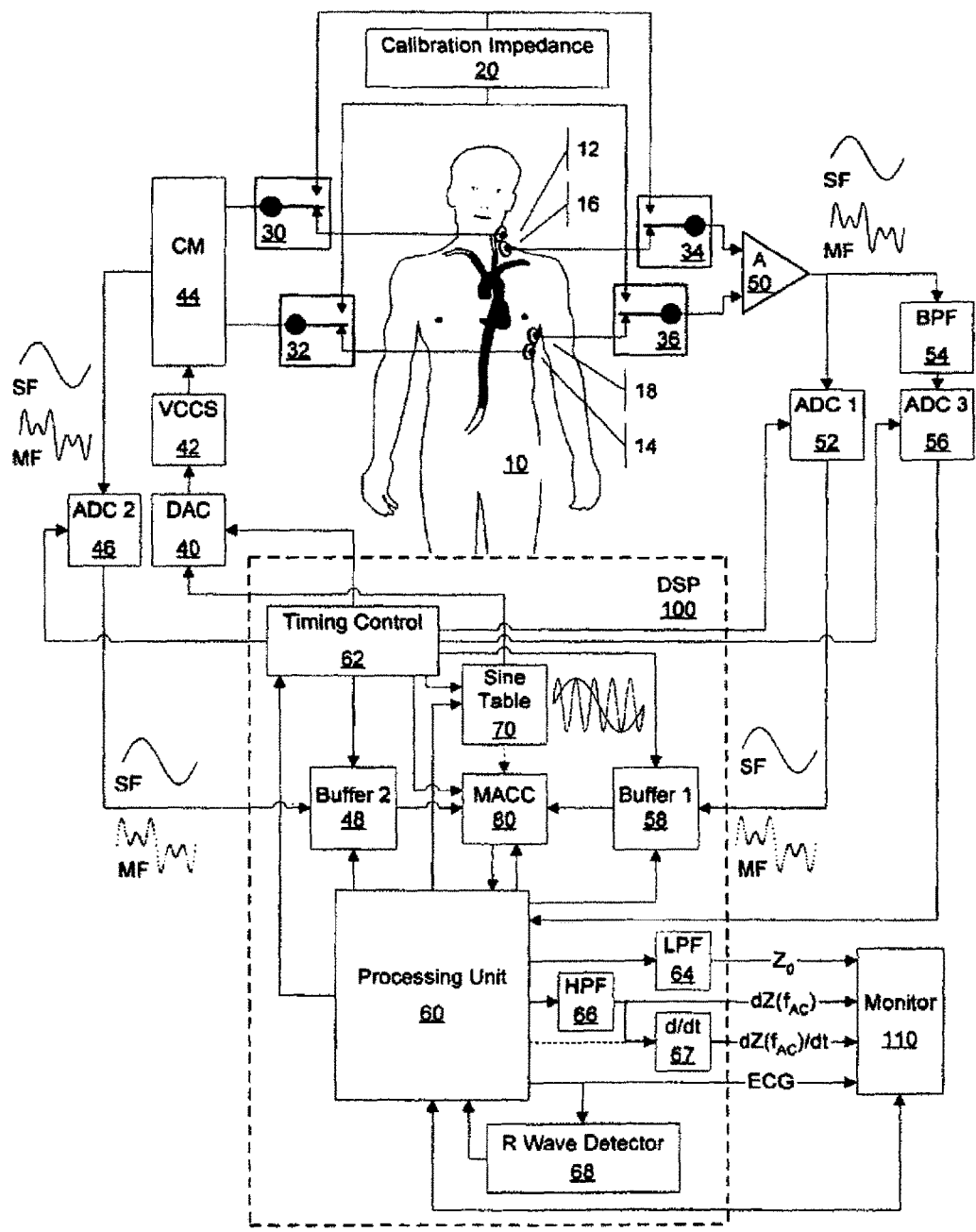
FIG. 1a is a basic diagram of an embodiment of the apparatus for application of a single or multi-frequency alternating current (AC) as the excitation signal, employing a single multiplier/accumulator (MACC) for digital demodulation of the resulting response signal, a voltage signal.

FIG. 1a illustrates a preferred embodiment of the apparatus according to the invention.

The embodiment is suitable for determining with high resolution the thoracic electrical impedance $$Z(f_{AC},t)=Z_0(f_{AC})+\Delta Z(f_{AC},t),$$

where:

$Z(f_{AC},t)$ is the thoracic electrical impedance (TEB), over time, for a particular frequency $f_{AC}$ of the alternating current (AC) applied, $Z_0(f_{AC})$ is the base impedance, i.e., the quasi-constant portion, or offset, of $Z(f_{AC},t)$, and $\Delta Z(f_{AC},t)$ is the change of thoracic electrical impedance, i.e., the portion of $Z(f_{AC},t)$ which is related to impedance changes during the cardiac cycle and respiration or ventilation cycle, A single or multi-frequency alternating current (AC) of known frequency and phase and having as an excitation source a constant amplitude is applied to an object 10 via a first pair of electrodes comprising a current electrode 12 located at the object's left side of the neck and a current electrode 14 located at the object's left side of the thorax, approximately at the level of the xiphoid process. Furthermore, a second pair of electrodes comprises a voltage sensing electrode 16, which is located below current electrode 12, and a voltage sensing electrode 18, which is located above current electrode 14. The second pair of electrodes 16 and 18 serves measuring the response signal across the object due to excitation with the alternating current (excitation signal) by means of the first pair of electrodes 12 and 14.

The alternating current (AC) can be switched to the object 10 or to a calibration impedance 20 via an electronic switch 30 and an electronic switch 32. Accordingly, a differential amplifier (A) 50 can be switched to the object 10 or the calibration impedance 20 via an electronic switch 34 and an electronic switch 36.

In the preferred embodiment, the alternating current (AC) is generated by the use of discrete samples of full sinusoidal waveforms or of portions thereof, the reference signal to the excitation signal, stored in an addressable sine table 70, which is connected to a digital-to-analog converter (DAC) 40. The samples in the sine table 70 are addressed in such a way that the digital-to-analog converter (DAC) 40 outputs a voltage signal of a desired frequency content and a desired voltage amplitude. The application of appropriate low pass filtering following the digital-to-analog converter (DAC) 40 in order to smooth possible ripples at its output is known to the art and not further described. A timing control 62 provides the addresses and clock signals required therefore. A processing unit 60 initializes the timing control 62 and the sine table 70.

The output of the digital-to-analog converter (DAC) 40 drives an excitation means embodied by a voltage-controlled current source (VCCS) 42, which generates an alternating current (AC) of the desired frequency content and of a constant AC amplitude. Typical, but not limited to, are AC frequencies in the range of 10 kHz to 200 kHz, and AC amplitudes in the range of 0.01 mA, preferably 2 mA, to 5 mA, the AC amplitudes of which are limited depending on the frequency of the alternating current (AC) applied. A current monitor (CM) 44 monitors the alternating current (AC) signal for the purpose of detection of saturation of the (excitation) current source due to overload or open circuitry and provides an analog signal reflecting the alternating current (AC) which is connected to a second fast analog-to-digital converter (ADC 2) 46. The alternating current (AC) applied from the excitation source is sampled and digitized by the second analog-to-digital converter (ADC 2) 46 at a sampling rate which is controlled by the timing control 62. The samples, further referred to as the Current Samples, are stored into a second buffer (Buffer 2) 48. The current monitor (CM) 44 and the second analog-to digital converter (ADC2) 46 together form a $2^{nd}$ measuring means, i.e. the measuring means for the excitation signal from the excitation source.

The application of the alternating current (AC) to the thorax causes a voltage between the response signal (voltage) sensing second pair of electrodes 16, 18. The differential amplifier 50 senses this voltage superimposed by the electrocardiogram (ECG), and amplifies it.

The current electrode 12 and the voltage sensing electrode 16, and the current electrode 14 and the voltage sensing electrode 18 may be each combined in a single double purpose electrode which serves to feed a current (excitation) signal and to retrieve a response signal.

The differential amplifier 50 is connected to a first fast analog-to-digital converter (ADC 1) 52, which digitizes the output of the differential amplifier 50 at a sampling rate preferably equal to the sampling rate of the second analog-to-digital converter (ADC 2) 46, both being controlled by the timing control 62. The digital samples obtained by the first analog-to-digital converter 52, further referred to as the Voltage Samples, are stored into a first buffer (Buffer 1) 58. Correlation, i.e., the process of multiplication and accumulation, is performed by a multiplier/accumulator (MACC) 80. The differential amplifier 50 and the first analog-to-digital converter (ADC1) 52 form a $1^{st}$ measuring means.

For obtaining a value proportional to the in-phase portion of a frequency $f_{AC}$ of the alternating current (AC) applied, the multiplier/accumulator (MACC) 80 correlates the Current Samples with samples of an ideal sinusoid of the frequency $f_{AC}$, which is obtained from the sine table 70 and represents the corresponding component of the alternating current (AC) applied. This process, also referred to as indirect correlation, is reiterated for each frequency $f_{AC}$ of the alternating current applied.

For obtaining a value proportional to the quadrature portion of a frequency $f_{AC}$ of the alternating current (AC) applied, the multiplier/accumulator (MACC) 80 correlates the Current Samples with samples of an ideal sinusoid of the frequency $f_{AC}$ shifted by −90 degrees in phase, which is obtained from the sine table 70. This process is reiterated for each frequency $f_{AC}$ of the alternating current applied.

For obtaining a value proportional to the in-phase portion of the sensed voltage at a frequency $f_{AC}$ of the alternating current (AC) applied, the multiplier/accumulator (MACC) 80 correlates the Voltage Samples with samples of an ideal sinusoid of the frequency $f_{AC}$, which is obtained from the sine table 70. This process is reiterated for each frequency $f_{AC}$ of the alternating current applied.

For obtaining a value proportional to the quadrature portion of the sensed voltage at a frequency $f_{AC}$ of the alternating current (AC) applied, the multiplier/accumulator (MACC) 80 correlates the Voltage Samples with samples of an ideal sinusoid of the frequency $f_{AC}$ shifted by −90 degrees in phase, which is obtained from the sine table 70. This process is reiterated for each frequency $f_{AC}$ of the alternating current applied.

Alternatively, in a single-frequency alternating current (AC) application, the multiplier/accumulator 80 correlates Current Samples with Voltage Samples directly, a process further referred to as direct correlation.

Alternatively, if the alternating current is kept at known constant amplitude, the measurement of the alternating current and the second analog-to-digital-converter (ADC 2) 46 and the second buffer (Buffer 2) 48 can be avoided. Then the samples of an ideal sinusoid obtained for each frequency from the sine table 70 (as the reference signal to the excitation signal) and used for correlation represent, for each frequency, the alternating current applied.

The differential amplifier 50 is connected to a filter 54 with band-pass characteristics and its output to a third analog-to-digital converter (ADC 3) 56, which samples the electrocardiogram (ECG). This separate ECG channel is advantageous not only for the detection of the intrinsic QRS complexes but also for the detection of cardiac pacemaker pulses if desired. The samples are acquired by the processing unit 60. The processing unit 60 applies one or more digital filters to the digitized electrocardiogram and provides this signal to a R-Wave detector 68, whose output is received by the processing unit 60.

In the preferred embodiment, the addresses of the sine table 70, the digital-to-analog converter (DAC) 40, the analog-to-digital converters (ADC) 46, 52, 56, and the buffers are synchronized with clock signals provided by the timing control 62. Because the current applied and the voltage measured are known exactly in frequency, amplitude and phase, errors due to system properties, such as propagations delays or phase shifts, can be effectively eliminated. Utilization of a calibration impedance, preferably a precision ohmic resistor, to which the system periodically switches, allows calibration before and in between measurements.

For each frequency $f_{AC}$ of the alternating current (AC) applied, the output of the correlation process is the digital demodulated waveform of the in-phase or quadrature portion of the thoracic electrical bioimpedance $Z(f_{AC},t)$ In the preferred embodiment, the second analog-to-digital converter (ADC 1) 46 and the first analog-to-digital converter (ADC 2) 52 are clocked at a rate significantly higher than the highest frequency of the alternating current (AC). As an example for a single-frequency (SF) alternating current (AC) application, but not limited to, the AC frequency is set to 50 kHz and the ADC sampling rates to 500 kHz. The correlation vector contains 2500 pairs. Thus, a correlation result is obtained every 5 ms, or 200 results per second. Doubling the ADC sampling rate would result in 400 correlation results per second.

The application of appropriate anti-aliasing filtering is known to the art and not further described.

The processing unit 60 initializes the timing control 62, the sine table 70 and the multiplier/accumulator (MACC) 80. It receives the output of the multiplier/accumulator (MACC) 80, and calculates the samples for thoracic electrical bioimpedance. The periodically occurring results of the correlation process form, for each frequency $f_{AC}$ of the alternating current (AC) applied, a digital waveform, which mirrors, within the scope of the embodiment according to FIG. 1a, the thoracic electrical bioimpedance $Z(f_{AC},t)$. The processing unit 60 aligns the digital waveforms of thoracic electrical bioimpedance and electrocardiogram (ECG) in time.

The application of an appropriate filter (LPF) 64 with low pass characteristics to $Z(f_{AC},t)$ produces a quasi-constant value, of which the amplitude is known as the base impedance, or $Z_0$.

The further application of an appropriate filter 66 with high pass characteristics (HPF) produces, for each frequency $f_{AC}$ of the alternating current (AC) applied, a waveform referred to as the change in impedance, in FIG. 1a referred to as $dZ(f_{AC})$. Depending on the filter applied, impedance changes due to respiration or ventilation may be isolated from impedance changes related to the cardiac cycle. Alternatively, the high pass filter is adapted, for example, to the heart rate in order to perform a separation of cardiac-related impedance changes from those related to respiration or ventilation at different physiological states, such as rest versus exercise, or adult versus pediatric or neonatal objects.

Impedance cardiometry, for instance, requires determination of the first time-derivative of the impedance signal. Either $\Delta Z(f_{AC},t)$ or directly $Z(f_{AC},t)$ (arrow with dotted line) is input to a differentiator 67. The output of the differentiator 67 is the rate of change of impedance $d\Delta Z(f_{AC})/dt$ or $dZ(f_{AC})/dt$, respectively, with $d\Delta Z(f_{AC})/dt$ and $dZ(f_{AC})/dt$ being equivalent.

Alternatively, the timing control 62, the sine table 70, the multiplier/accumulator (MACC) 80, the buffers 48, 58, the processing unit 60 and the filters 62, 64, the R-Wave detector 68, or a part thereof, are integrated into the program of a digital signal processor (DSP) 100 or a hardwired processor (not shown) or a fixed programmable gate array (FPGA)

(not shown). The digital waveforms $Z_0(f_{AC})$, $\Delta Z(f_{AC},t)$ and the electrocardiogram (ECG), or a subset thereof, are input to a Cardiometry Monitor 110 in addition to data lines synchronizing the communication and information between processing unit 60, or digital signal processor 100, and a Cardiometry Monitor 110.

Alternatively, the cardiometry monitor (110) receives the bioimpedance waveform $Z(f_{AC},t)$ and processes the signals $Z_0(f_{AC})$, $\Delta Z(f_{AC},t)$ and $dZ(f_{AC})/dt$.

In the event the object 10 is switched to the voltage-controlled current source (VCCS) 42 and to the differential amplifier 50, the demodulated signal consists of a voltage portion related to the electrical impedance obtained from the object 10 and the electrocardiogram (ECG). Otherwise, the demodulated signal represents the value of the calibration impedance 20. The use of a calibration impedance is an option to eliminate the influence of electrical circuit properties on measurements. Preferably, the calibration impedance consists of an ohmic resistor. In the event of a complex calibration impedance, the frequency-dependent phase must be considered appropriately in the calculation of the object impedance.

Alternatively, the apparatus of the invention is applicable to other areas of the object 10, such as for example the limbs in order to determine peripheral blood volume changes.

Other embodiments according to the apparatus of the invention include the replacement of the voltage-controlled current source by a voltage source including a current measuring circuit.

Another embodiment relies on the discrete values of a sine waveform stored in the sine table 70 and the accuracy of the constant amplitude of the alternating current (AC) applied instead of measuring the alternating current (AC) signal.

Another embodiment determines the electrical admittance $$Y(f_{AC},t)=Y_0(f_{AC})+\Delta Y(f_{AC},t)$$

where $Y(f_{AC},t)$ is the thoracic electrical bioadmittance, $Y_0(f_{AC})$ is the base admittance, i.e., the quasi-constant part, or offset, of $Y(f_{AC},t)$ $\Delta Y(f_{AC},t)$ is the change in thoracic electrical bioadmittance, i.e., the part of $Y(f_{AC},t)$ which is related to conductance changes during the cardiac cycle and the respiration or ventilation cycle, instead of the electrical bioimpedance $Z(f_{AC},t)$, thus, obtaining the base admittance $Y_0(f_{AC})$, the change in bioadmittance $\Delta Y(f_{AC},t)$ and the rate of change in bioadmittance $dY(f_{AC})/dt$.

Another embodiment determines the complex impedance by separating the in-phase and the quadrature portion of the impedance (or admittance) with separate correlation processes.

Figure 1B:
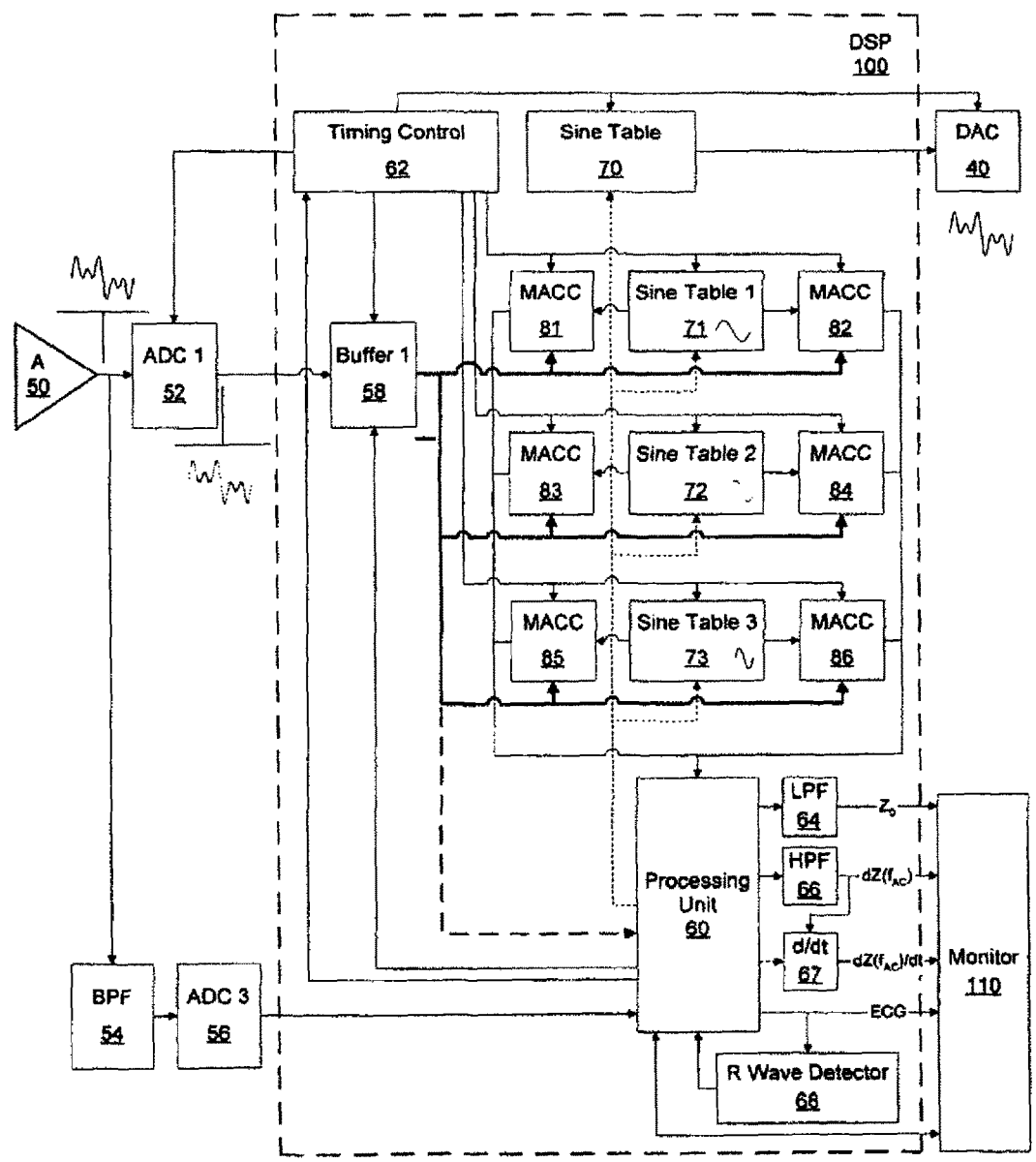
FIG. 1b is a basic diagram of an embodiment of the apparatus for application of an alternating current containing 3 frequency components as the excitation signal, employing a multiplier/accumulator (MACC) for parallel digital demodulation of each frequency component of the resulting response signal, a voltage signal.

Another embodiment applies a set of alternating current (AC) frequencies (further referred to as multi-frequency, or MF application), instead of a single frequency (further referred to as SF application) to the object 10 and utilizes a set of frequency-sensitive demodulation processes, see FIG. 1*b*.

The placement of pairs of current application electrodes and pairs of voltage sensing electrodes is not limited to the placement shown in FIG. 1.

The current electrode 12 may be moved from the left side of the object's neck to the forehead and the current electrode 14 may be moved from the left side of the thorax, approximately at the level of the xiphoid process, to the left leg. A current application electrode placement where the current application electrode 12 is moved from the left side of the object's neck to the forehead and the current application electrode 14 is moved from the left side of the thorax to the left leg is also feasible. This kind of electrode placement may be advantageous in applications to pediatric or neonatal objects 10, where space to place electrodes is sometimes limited.

Alternatively, the neck electrodes 12, 16 are located at the right side of the object 10 instead of the left side (as illustrated in FIG. 1). Alternatively, the neck current electrode may be applied to the forehead. The current electrode 14 may be applied either to the thorax, approximately at the level of the xiphoid process, or to the left leg. This kind of electrode placement may be advantageous in applications to pediatric or neonatal objects 10, where space to place electrodes is sometimes limited.

Alternatively, the pair of neck electrodes is integrated into one electrode applying the current and sensing the voltage. Alternatively, the pair of thorax electrodes is integrated into one electrode.

Furthermore, instead of using a first electrode array with the four electrodes 12, 14, 16, 18 on the left side of the object 10 only, a second electrode array is placed on the right side of the object 10 (not shown), and the application of the alternating current (AC) and the voltage measurement is performed using the first and the second electrode array. Likewise the previous electrode setups, a pair of current application and voltage sensing electrodes may be integrated into one electrode.

For esophageal applications, the electrodes can be located as electrodes onto an esophageal catheter or probe (not shown) or tracheal tube (not shown).

For invasive applications, the electrodes can be integrated into aortic grafts or, in combination with cardiac pacemakers or defibrillators, into pacing or defibrillation leads, or other implants which remain in the body of the object.

FIG. 1*b* illustrates an embodiment similar to the embodiment of FIG. 1*a* except for an implementation of a parallel in-phase and quadrature demodulation process aimed at the three different frequency contents of the measured voltage signal measured by the differential amplifier (A) 50 and digitized by a first analog-to-digital converter (ADC) 52. The embodiment of FIG. 1*b* applies an alternating current (AC), which consists of three different frequencies $f_1$, $f_2$, and $f_3$, each of which is applied at a constant amplitude. The alternating current (AC) applied is not measured but each frequency component represented, in frequency and phase, by a first sine table 71, a second sine table 72 and a third sine table 73. In the multi-frequency (MF) alternating current (AC) embodiment, demodulation must be performed for each applied frequency $f_{AC}$ separately.

A first MACC 81 accumulates the products of the sampled values measured, amplified and digitized by the ADC 52 and the reference sine values of the first frequency $f_1$ stored in the first sine table 71, calculating as a result a value proportional to the in-phase portion, or real part of the impedance at the first frequency $f_1$.

A second MACC 82 accumulates the products of the sampled values measured, amplified and digitized by the ADC 52 and the reference cosine values of the first frequency $f_1$ stored in the first sine table 71, producing as a result a value proportional to the quadrature portion, or imaginary part of the impedance at the first frequency $f_1$.

A third MACC 83 accumulates the products of the sampled values measured, amplified and digitized by the ADC 52 and the reference sine values of the second frequency $f_2$ stored in the second sine table 72, producing as a result a value proportional to the in-phase portion, or real part of the impedance at the second frequency $f_2$.

A fourth MACC 84 accumulates the products of the sampled values measured, amplified and digitized by the ADC 52 and the reference cosine values of the second frequency $f_2$ stored in the second sine table 72, producing as a result a value proportional to the quadrature portion, or imaginary part of the impedance at the second frequency $f_2$.

A fifth MACC 85 accumulates the products of the sampled values measured, amplified and digitized by the ADC 52 and the reference sine values of the third frequency $f_3$ stored in the third sine table 73, producing as a result a value proportional to the in-phase portion, or real part of the impedance at the third frequency $f_3$.

A sixth MACC 86 accumulates the products of the sampled values measured, amplified and digitized by the ADC 52 and the reference cosine values of the third frequency $f_3$ stored in the third sine table 73, producing as a result a value proportional to the quadrature portion, or imaginary part of the impedance at the third frequency $f_3$.

While the embodiment shows a parallel process of multiplication and accumulation, the process may be serialized by implementing memory in order to store intermediate results. More advantageously, the timing control 62, the processing unit 60, the sine tables 71, 72, 73 and multiplier/accumulators (MACC) 81, 82, 83, 84, 85, 86 are incorporated into a digital signal processor (DSP) 100 or into a hard-wired processor or into a fixed programmable gate array (FPGA).

FIG. 1c-1g illustrate the application of a multi-frequency alternating current (AC) application.

For an example, the alternating current (AC) signal outputted by the voltage-controlled current source (VCCS) 42 shall consist of three different sinusoidal signals $$S_i(t) = A_i \cdot \sin(2\pi f_i)t$$

of a first frequency $f_1$, a second frequency $f_2$ and a third frequency $f_3$. In this example, the second frequency is three times the frequency of the first frequency, i.e, $$f_2 = 3 \cdot f_1$$

and the third frequency is five times the frequency of the first frequency, i.e., $$f_3 = 5 \cdot f_1.$$

Figure 1C:
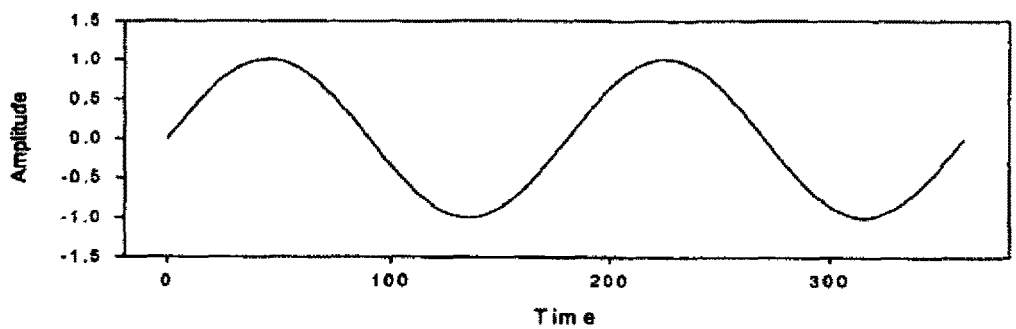
FIG. 1c-1g illustrate the details of embodiments employing a multi-frequency alternating current (AC) application.
Figure 1D:
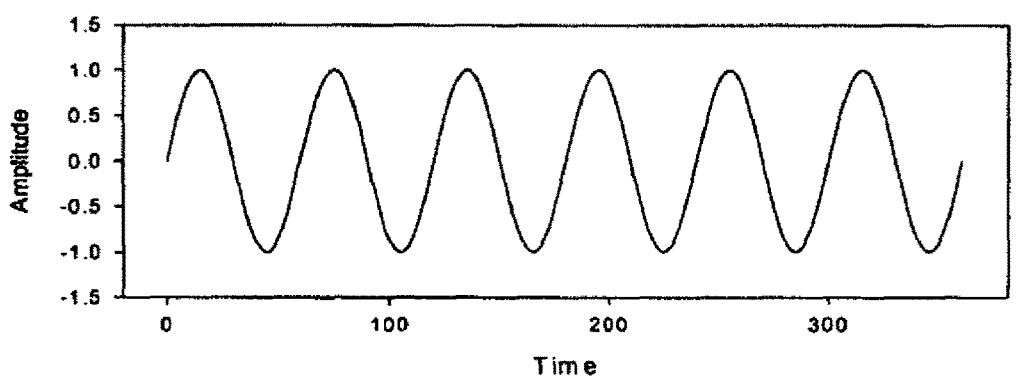
Figure 1E:
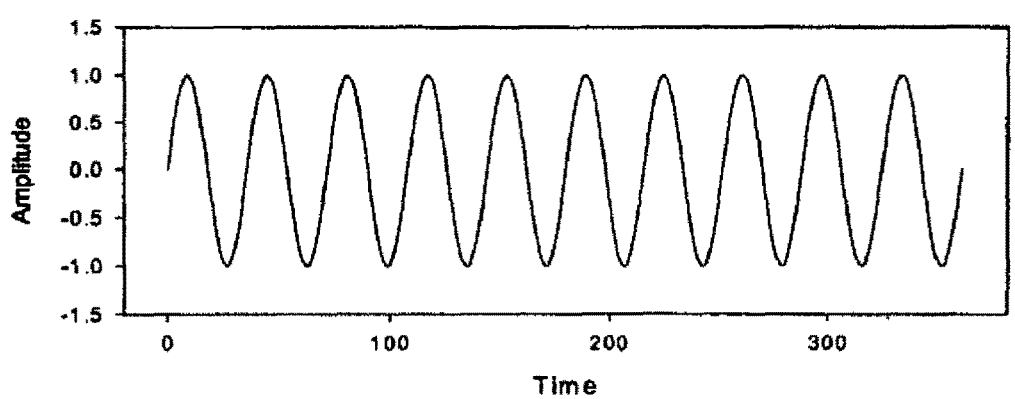

FIG. 1c illustrates the signal of the first frequency over a time. FIG. 1d illustrates the signal of the second frequency over the same time. FIG. 1e illustrates the signal of the third frequency over the same time. For simplification, all signals are shown with the same amplitude $A_i$ normalized at 1.

Figure 1F:
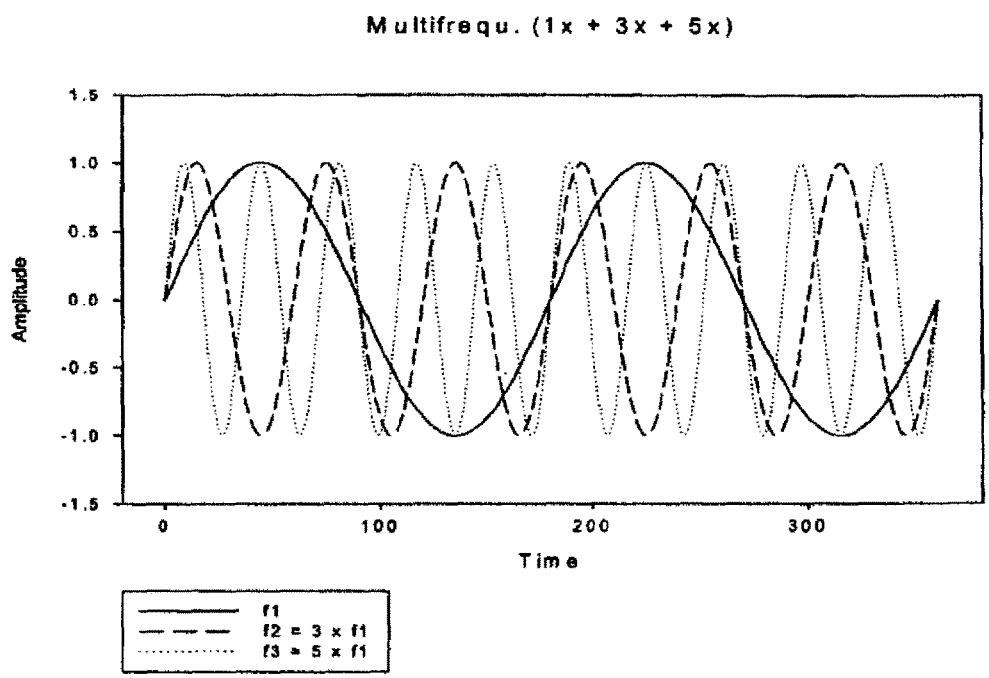

FIG. 1f superimposes the three signals $S_i(t)$ in the same diagram. The frequencies and their phases are chosen in such a way that within the given window the signal begin and end at zero crossings.

Figure 1G:
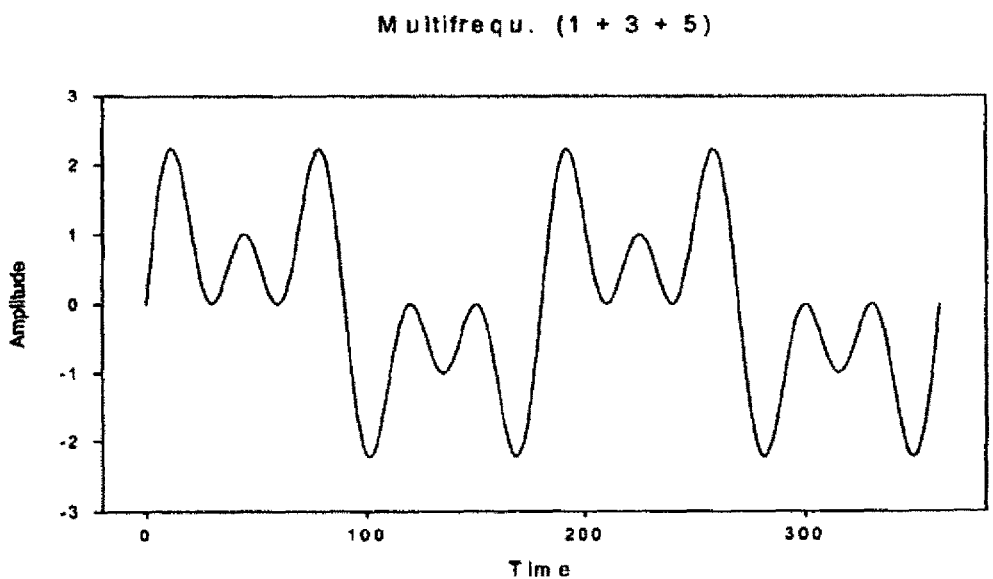

The sum of the three signals, i.e.

$$S(t) = \sum_{i=1}^{3} A_i \cdot \sin(2\pi f_i)t$$

is shown in FIG. 1g.

Figure 2A:
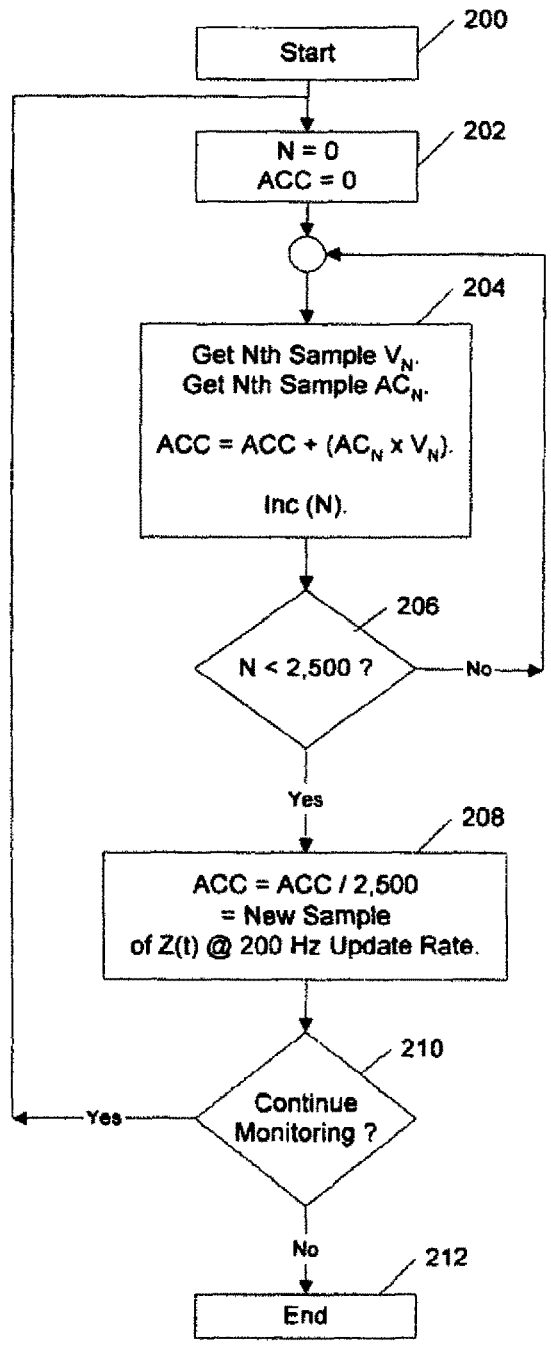
FIG. 2a is a flowchart of one embodiment of a correlation method.

FIG. 2a provides a flow chart of the correlation process for a preferred embodiment, without being limited to it.

In this embodiment, as an example, but not limited to, the in-phase portion I(Z(t)) of the complex impedance at a single frequency (SF) of $f_{AC}$=50 KHz is of interest. Furthermore, the alternating current (AC) applied is not measured but held constant. Accordingly, the voltage due to the alternating current (AC) application is proportional to the impedance Z(t).

A sine table 70 (FIG. 1a) is set up in such a way that its contents represents, in digital values, the alternating current (AC) amplitudes at all times. For measuring the voltage due to the alternating current (AC) application, the embodiment utilizes the first analog-to-digital converter (ADC) 52 operating at a sampling rate of 500 kHz. In order to achieve, for example, an update rate of the impedance signal of 200 Hz, i.e., a new value for Z(t) every 5 ms, the correlation vector must include $$N_{CORR} = \frac{500 \text{ KHz}}{200 \text{ Hz}} = 2,500$$

correlation pairs. Each pair consists of a digitized voltage sample and a corresponding digital value in the sine table, of which the digital value represents the amplitude of the alternating current at the time of the voltage sampling.

At the beginning of the correlation process 200, the correlation counter N and the accumulator ACC are reset by circuit 202.

The multiplier obtains the first digitized voltage sample $V_0$ (acquired by the first analog-to-digital converter (ADC) 52 and the corresponding first digital value provided by the sine table (representing the alternating current (AC) applied), and calculates the product 204 thereof. The product is added to the accumulator.

Then the multiplier obtains the second digitized voltage sample (acquired by the ADC) and the corresponding second digital value provided by the sine table (representing the alternating current (AC) applied), calculates the product thereof and adds the product to the accumulator 204. This process is reiterated by circuit 206 until the total number of desired correlation pairs is reached (in this embodiment, the correlation vector contains 2,500 correlation pairs).

After multiplying and accumulating the 2,500 correlation pairs, the content of the accumulator is normalized by normalizer 208 by dividing the result in the accumulator by the number of pairs N which contributed to the result.

This normalized result is the result of the correlation process and represents one discrete sample of the Z(t) waveform. Consecutive correlation processes are executed until decision circuit 210 blocks reiteration and monitoring is terminated at 212.

In the event the quadrature portion Q(Z(t)) of the impedance is of interest, correlation is performed of the samples obtained by the first analog-to-digital converter (ADC) 52 with a digitized sinusoidal waveform shifted in phase by 90 degrees, i.e., a digitized cosine waveform (not shown).

In the event the magnitude of the impedance is of interest, the in-phase portion I(Z(t)) and quadrature portion Q(Z(t)) of the impedance are determined and added (as vectors). Alternatively, the magnitude of the impedance can be obtained by performing multiple correlation processes, which differ in the phase shifts applied to the sinusoid digitized waveform, the ADC samples are correlated with. For example, the phase shift can be varied between −90 degrees and +90 degrees in steps of 1 degree. A correlation process is performed for each phase shift (a feasible task for a digital signal processor). The correlation with the phase shift providing the maximum result equates (or is proportional at least) to the impedance magnitude.

The ADC sampling rate of 500 kHz and the Z(t) update rate of 200 Hz is an example for an embodiment, and not limited to it. In another example an ADC sampling rate of 1 MHz in the event an Z(t) update rate of 400 Hz is specified (not shown).

Figure 2B:
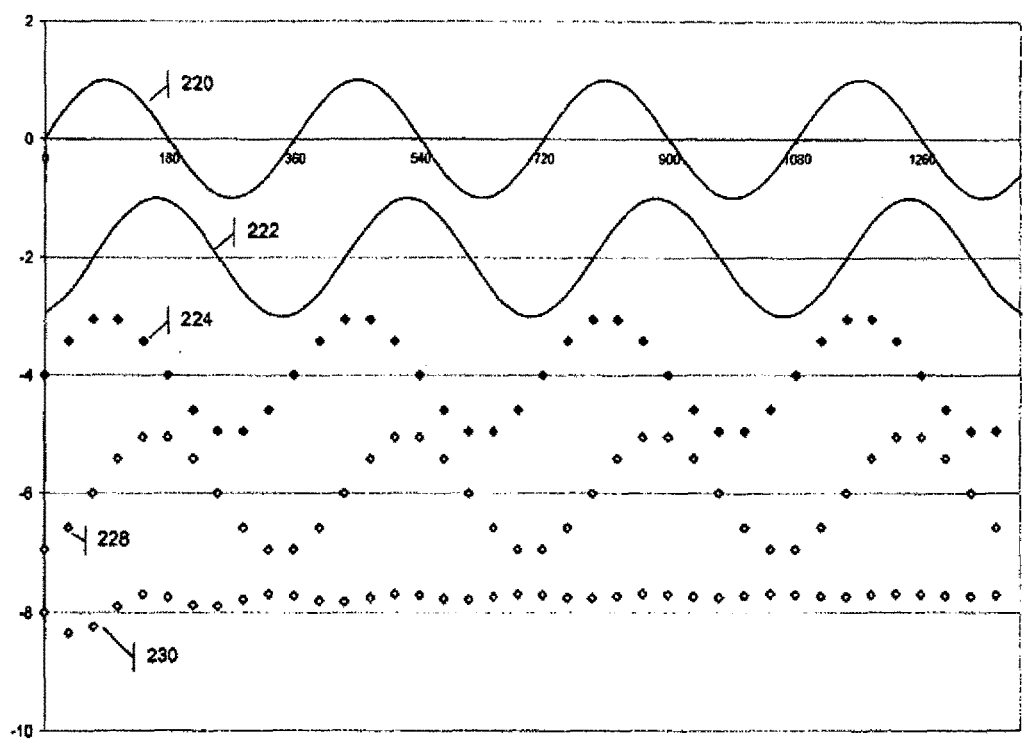

FIG. 2b provides a chart which graphically explains the correlation process for the preferred embodiment of FIG. 2a.

The horizontal axis is defined as the time axis. An analog waveform 220 represents the alternating current (AC), which is generated by the voltage-controlled current source (VCCS) 42. An analog waveform 222 represents the analog voltage signal, which is sensed by the differential amplifier 50. The analog waveform 222 is considered as an example and may vary in amplitude and phase depending on the actual impedance measured.

A digitized waveform 224 represents the discrete values of the alternating current (AC), which are stored in the sine-table 70 or obtained through (current) measurement.

A digitized waveform 228 is the output of the first analog-to-digital converter (ADC) 52 digitizing the sensed voltage.

A digitized waveform 230 represents the results of the correlation process at each point in time. FIG. 2b illustrates 4 cycles of the AC frequency only. The number of cycles over which correlation is performed is determined by design requirements. The aforementioned preferred embodiment, which specifies a Z(t) update rate of 200 Hz, generates an AC frequency of 50 kHz and utilizes an ADC sampling rate of 500 kHz, performs correlation over 2500 cycles to generate one point of the function Z(t), i.e. one sample of the electrical impedance over time.

FIG. 3 provides an overview over possible embodiments of the invention. These embodiments can be differentiated into whether or not a calibration impedance is used, whether or not the alternating current (AC) applied is measured, whether direct or indirect correlation is performed, and/or whether or not the measured signals are fitted with ideal waveforms.

Figure 4A:
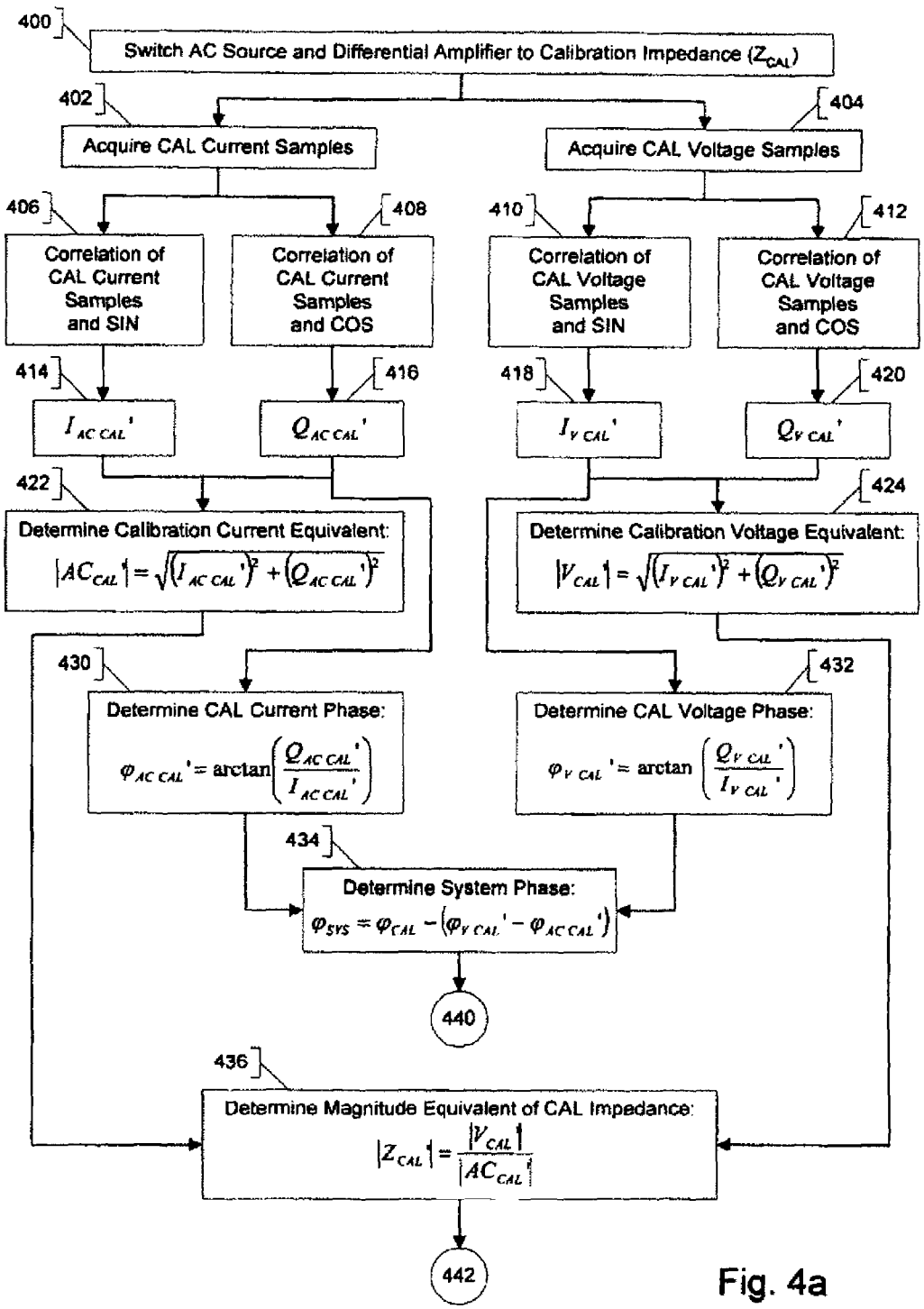
FIGS. 4a and 4b form jointly a flowchart of a first embodiment of the invention for the determination of the complex object impedance ($Z_{OBJ}$), i.e., the impedance of interest, by measurements of the alternating current (AC) as an excitation signal and the alternating voltage as the response signal, and the use of a calibration impedance, and by application of indirect correlation.
Figure 4B:
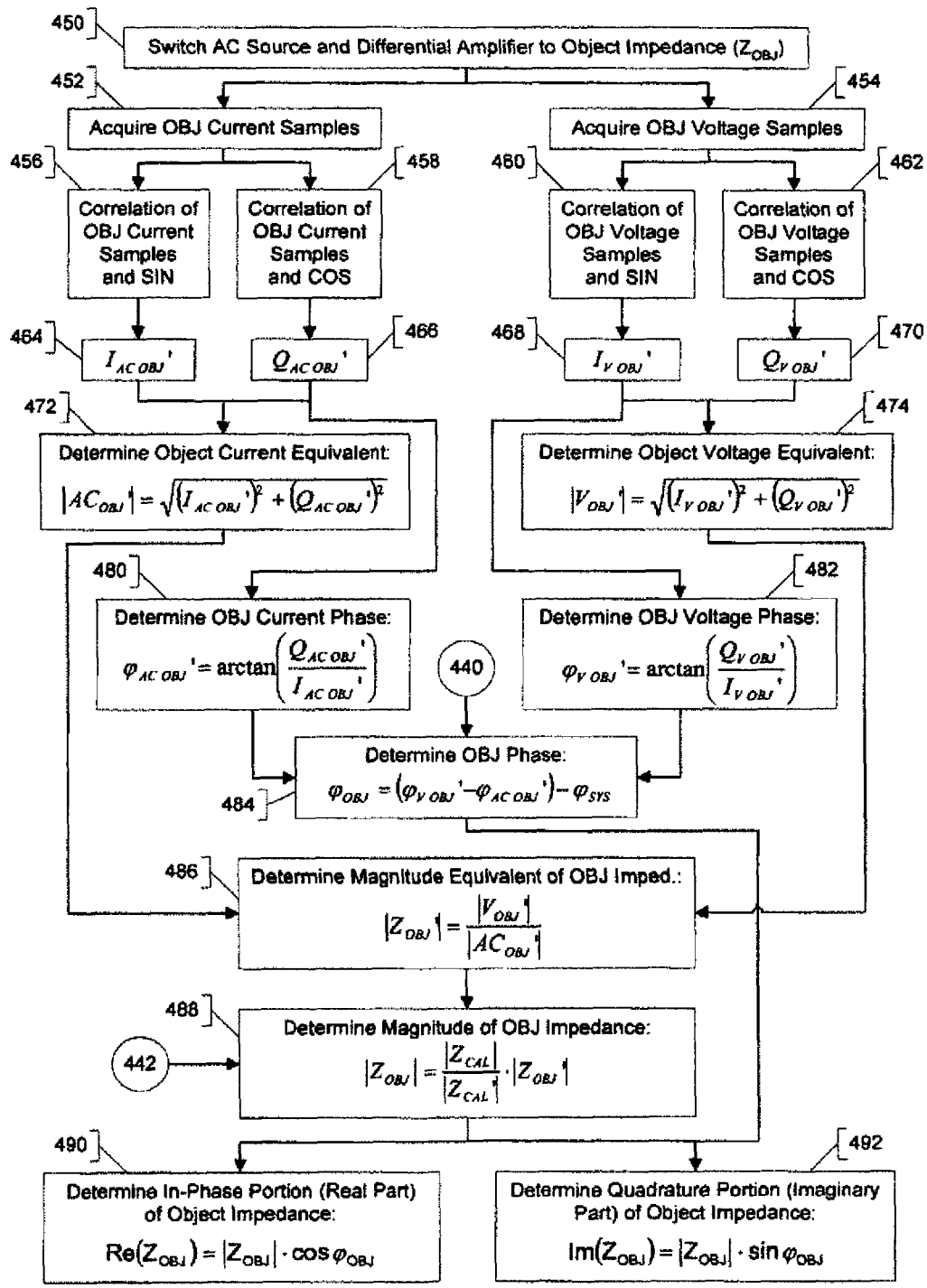

According to a first embodiment, FIGS. 4a and 4b, the voltage controlled current source (VCCS) 42, which generates a single frequency (SF) or multi-frequency (MF) alternating current (AC), and the differential amplifier (A) 50 are switched to the calibration impedance 20, and the alternating current (AC) applied and the resulting voltage are measured, amplified and digitized.

In the event of a single frequency (SF) alternating current (AC) application, because the frequency of the measured alternating current (AC) applied and, thus, of the voltage measured is known, the samples measured, amplified and digitized can be fitted towards discrete values of an ideal sinusoidal waveform using commonly known fitting processes.

Then, in a process further referred to as indirect correlation, for each frequency $f_{AC}$ of the alternating current (AC) applied, the amplified, digitized and optionally fitted samples obtained from the measurement of the alternating current (AC) applied are correlated with the discrete values of an ideal sine waveform in order to obtain a value proportional to the in-phase portion $I_{AC}(f_{AC})$ of the alternating current (AC) and are correlated with the discrete values of an ideal cosine waveform in order to obtain a value proportional to the quadrature portion $Q_{AC}(f_{AC})$ of the alternating current (AC).

Furthermore, for each frequency $f_{AC}$ of the alternating current (AC) applied, the amplified, digitized and optionally fitted samples obtained from the measurement of the voltage are correlated with the discrete values of an ideal sine waveform in order to obtain a value proportional to the in-phase portion $I_V(f_{AC})$ of the voltage and correlated with the discrete values of an ideal cosine waveform in order to obtain a value proportional to the quadrature portion $Q_V(f_{AC})$ of the voltage.

Thereafter, the aforementioned processes are performed with the current source and the differential amplifier (A) 50 switched to the object 10.

A more detailed description of this embodiment is given below in connection with the description of FIGS. 4a and 4b.

Figure 5:
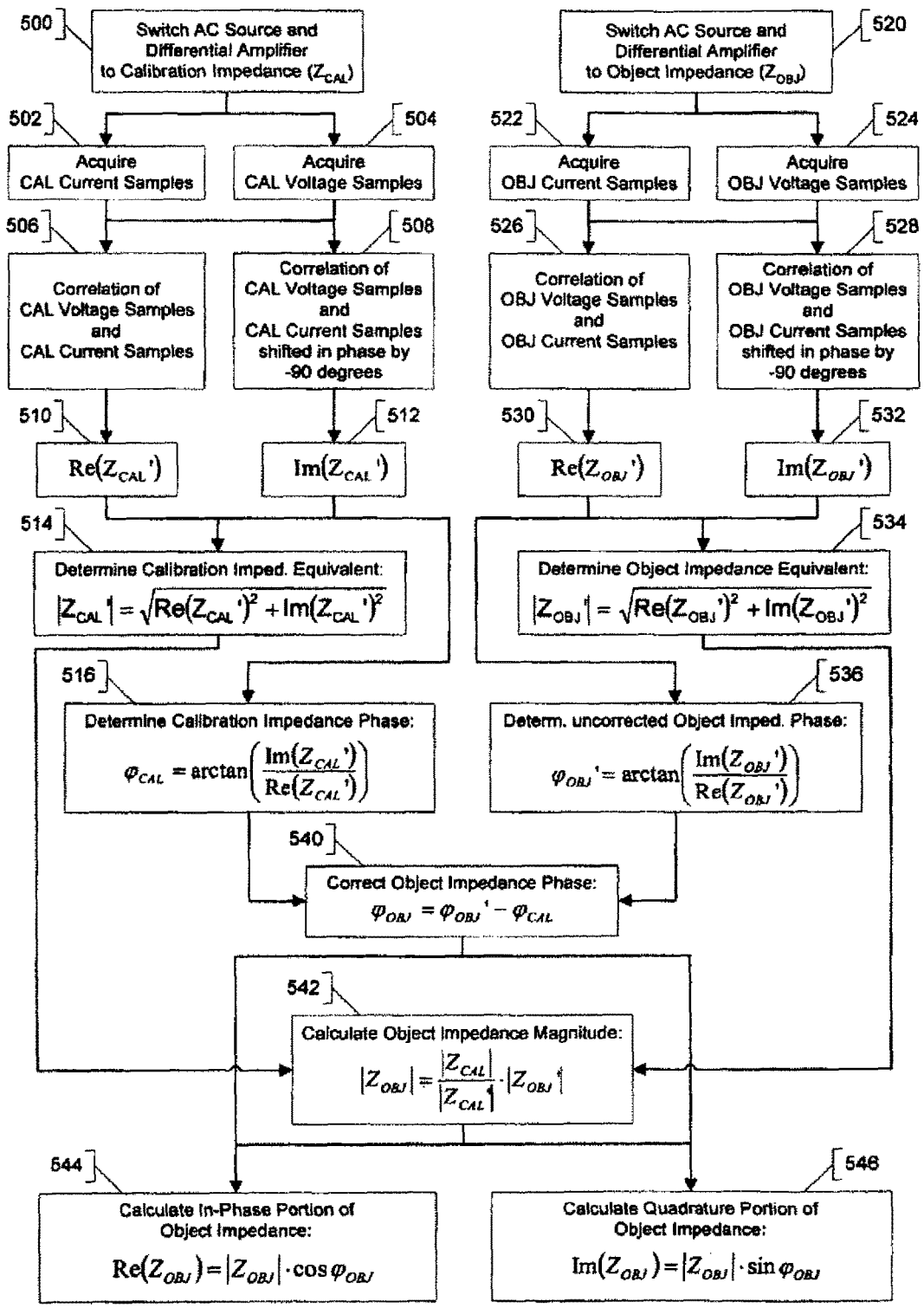
FIG. 5 is a flowchart of a second embodiment for the determination of the complex object impedance ($Z_{OBJ}$), i.e., the impedance of interest, by measurements of the alternating current (AC) as the excitation signal and the alternating voltage as the response signal, and the use of a calibration impedance, and by application of direct correlation.

According to a second embodiment, FIG. 5, the voltage controlled current source (VCCS) 42, which generates a single-frequency (SF) alternating current (AC), and the differential amplifier (A) 50 are switched to the calibration impedance 20, and the alternating current (AC) applied and the resulting voltage are measured, amplified and digitized.

Because the frequency of the alternating current (AC) applied and, thus, of the voltage measured is known, the samples obtained, amplified and digitized can be fitted towards discrete values of an ideal sinusoidal waveform using commonly known fitting processes.

Then, in a process further referred to as direct correlation, the amplified, digitized and optionally fitted samples obtained from the measurement of the voltage and obtained from the measurement of the alternating current (AC) applied are correlated.

Thereafter, the aforementioned processes are performed with the current source (VCCS) 42 and to the differential amplifier 50 switched to the object 10.

A more detailed description of this embodiment is given below with FIG. 5.

Figure 6:
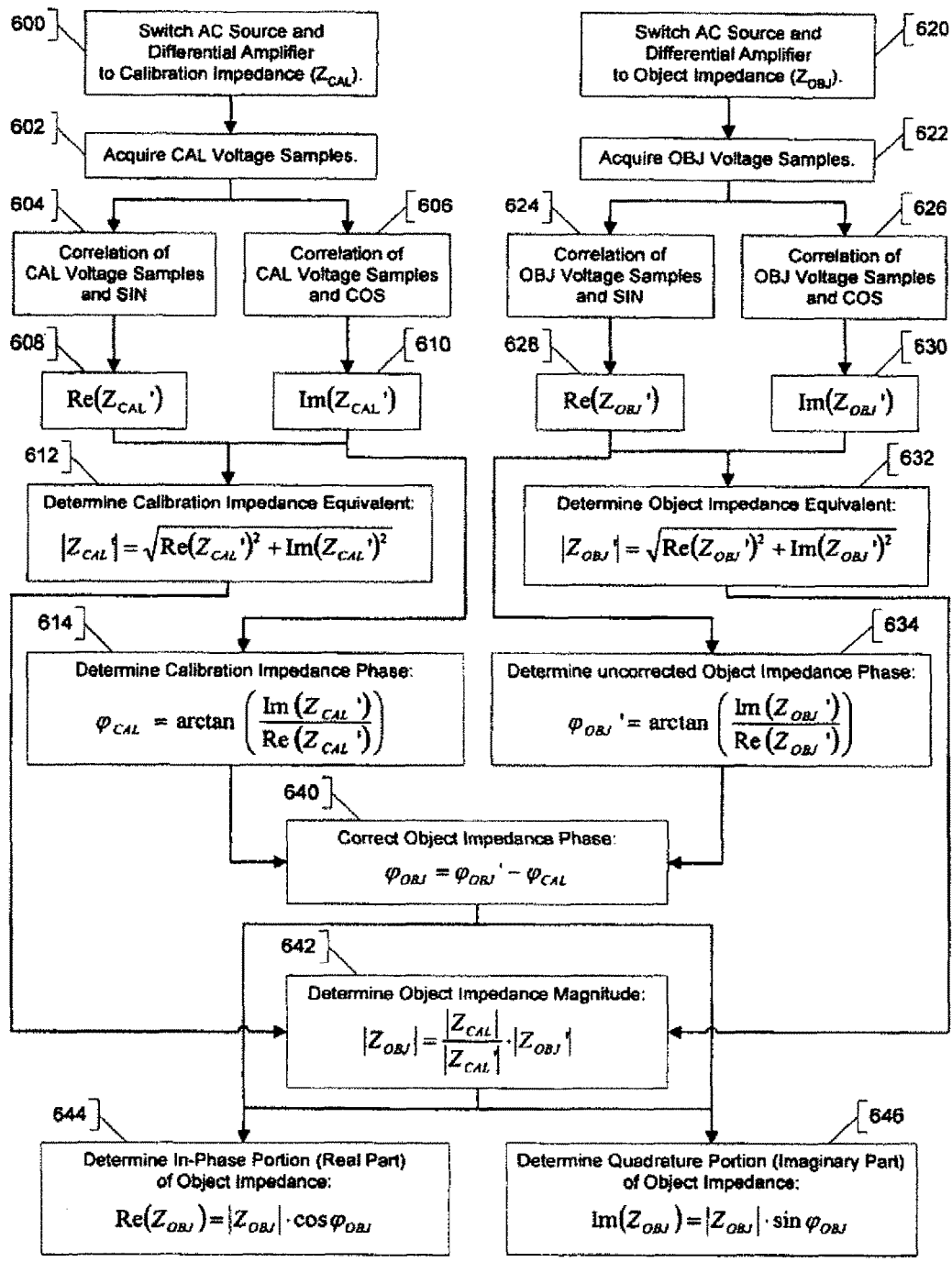
FIG. 6 is a flowchart of a third embodiment for the determination of the complex object impedance ($Z_{OBJ}$), i.e., the impedance of interest, with the measurement of the alternating voltage but without the measurement of the alternating current (AC) applied and with the use of a calibration impedance.

According to a third embodiment, FIG. 6, the voltage controlled current source (VCCS) 42, which generates a single frequency (SF) or multi-frequency (MF) alternating current (AC), and the differential amplifier (A) 50 are switched to the calibration impedance 20 but only the resulting voltage is measured, amplified and digitized.

In the event of a single frequency (SF) alternating current (AC) application, because the frequency of the alternating current (AC) applied and, thus, the frequency of the measured voltage is known, the samples obtained, amplified and digitized can be fitted towards discrete values of an ideal sinusoidal waveform using commonly known fitting processes.

Then, for each frequency $f_{AC}$ of the alternating current (AC) applied, the amplified, digitized and optionally fitted samples obtained from the voltage measurement are correlated with the discrete values of an ideal sine waveform in order to obtain a value proportional to the in-phase portion $I_V(f_{AC})$ of the voltage and correlated with the discrete values of an ideal cosine waveform in order to obtain a value proportional to the quadrature portion $Q_V(f_{AC})$ of the voltage.

Thereafter, the aforementioned processes are performed with the alternating current (AC) source 42 and the differential amplifier (A) 50 switched to the object 10.

A more detailed description of this embodiment is given below with FIG. 6.

Figure 7:
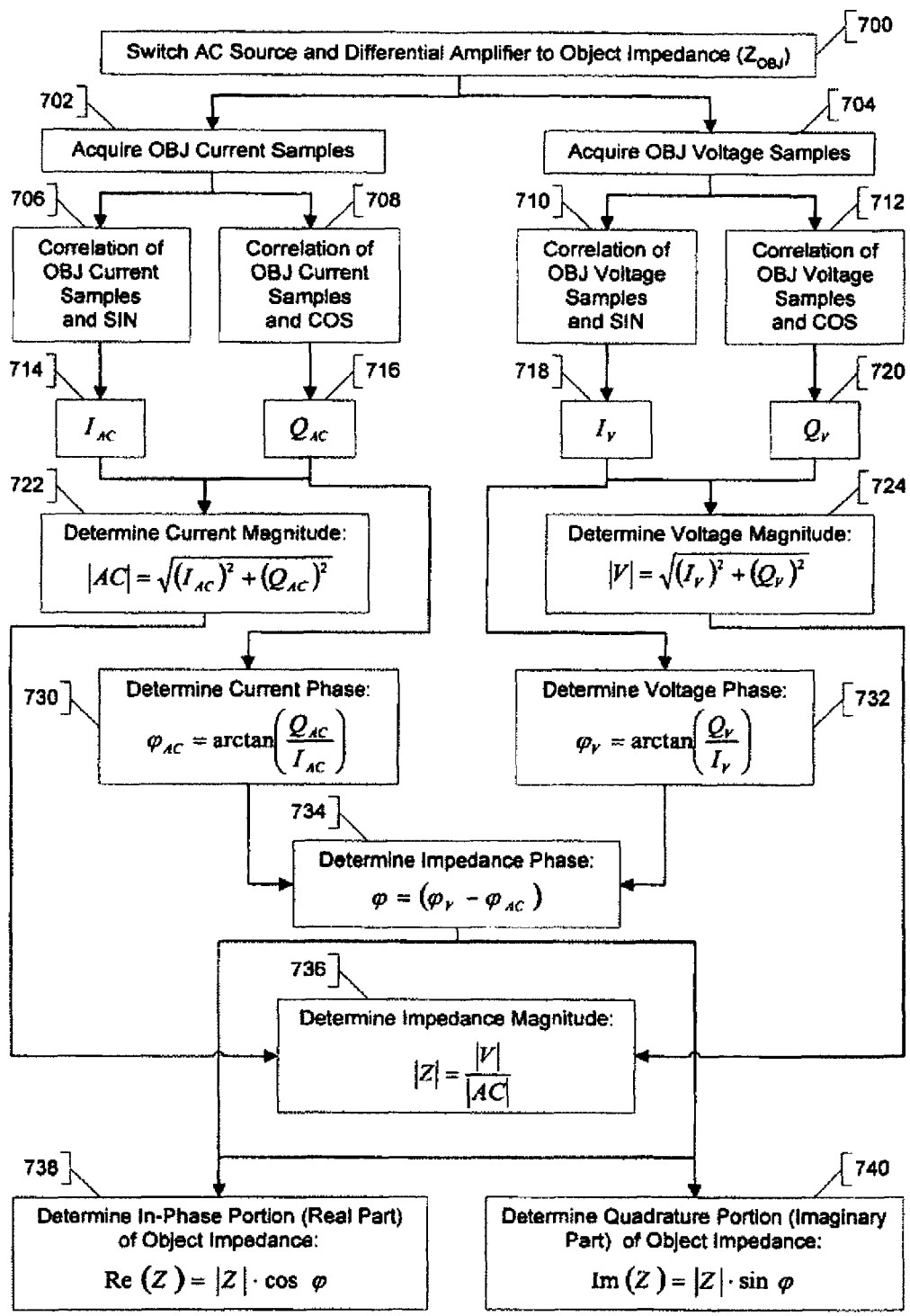
FIG. 7 is a flowchart of a fourth embodiment for the determination of the complex object impedance (Z), i.e., the impedance of interest, by measurements of the alternating current (AC) and the alternating voltage, without the use of any calibration impedance, and by application of indirect correlation.

According to a forth embodiment, FIG. 7, the voltage controlled current source (VCCS) 42, which generates a single frequency (SF) or multi-frequency (MF) alternating current (AC), and the differential amplifier (A) 50 are switched to the object 10, and the alternating current (AC), the excitation signal, applied and the resulting voltage, the response signal, are measured/acquired, amplified and digitized.

In the event of a single frequency (SF) alternating current (AC) application, because the frequency of the alternating current (AC) applied and, thus, of the voltage measured is known, the samples obtained, amplified and digitized can be fitted towards discrete values of an ideal sinusoidal waveform using commonly known fitting processes.

Then, in a process further referred to as indirect correlation, for each frequency $f_{AC}$ of the alternating current (AC) applied, the amplified, digitized and optionally fitted samples obtained from the measurement of the alternating current (AC) applied are correlated with the discrete values of an ideal sine waveform in order to obtain a value proportional to the in-phase portion $I_{AC}(f_{AC})$ of the alternating current (AC) and correlated with the discrete values of an ideal cosine waveform in order to obtain a value proportional to the quadrature portion $Q_{AC}(f_{AC})$ of the alternating current (AC).

Furthermore, for each frequency $f_{AC}$ of the alternating current (AC) applied, the amplified, digitized and optionally fitted samples obtained from the voltage measurement are correlated with the discrete values of an ideal sine waveform in order to obtain a value proportional to the in-phase portion $I_V(f_{AC})$ of the voltage and correlated with the discrete values of an ideal cosine waveform in order to obtain a value proportional to the quadrature portion $Q_V(f_{AC})$ of the voltage.

A more detailed description of this embodiment is given below with FIG. 7.

Figure 8:
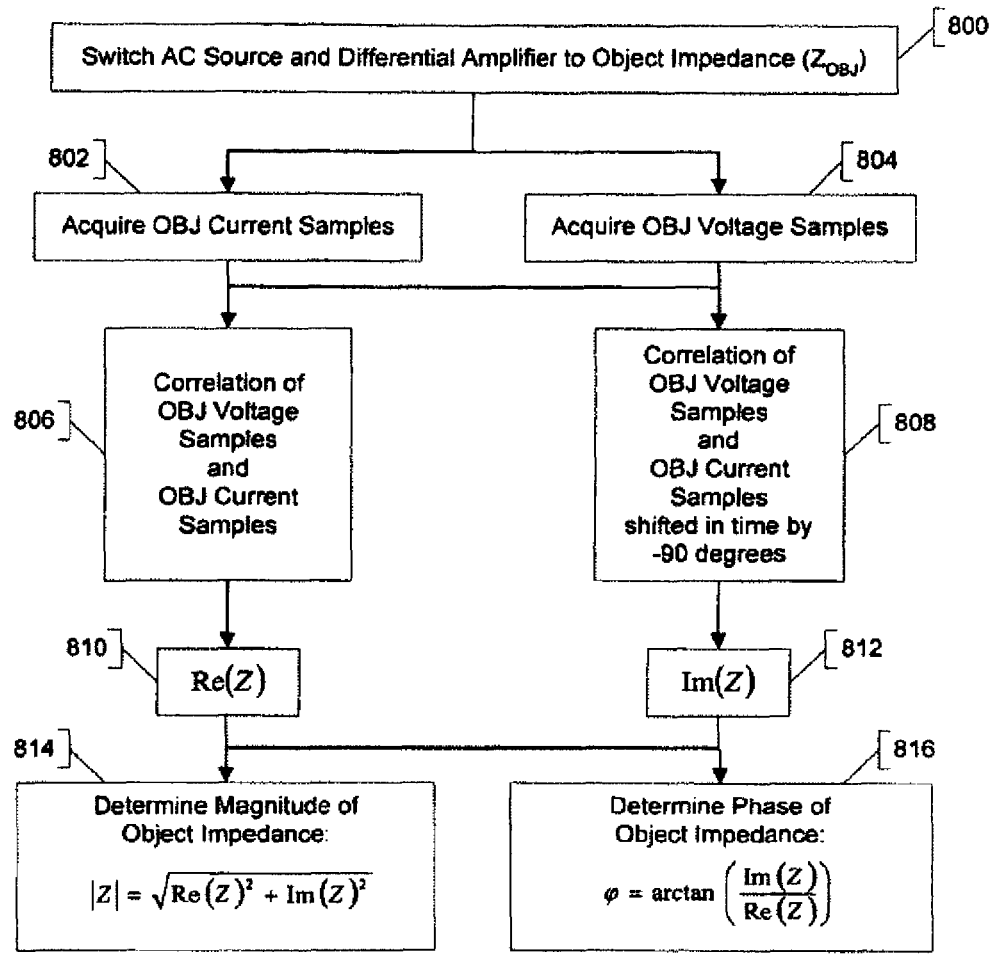
FIG. 8 is a flowchart of a fifth embodiment for the determination of the complex object impedance (Z), i.e., the impedance of interest, by measurements of the alternating current (AC) and the alternating voltage, without the use of any calibration impedance, and by application of direct correlation.

According to a fifth embodiment, FIG. 8, the voltage controlled current source (VCCS) 42, which generates a single-frequency (SF) alternating current (AC), and the differential amplifier (A) 50 are switched to the object 10, and the alternating current (AC), the excitation signal, applied and the resulting voltage, the response signal, are measured/acquired, amplified and digitized.

Because the frequency of the excitation signal and of the response signal is known, the samples acquired, amplified and digitized can be fitted towards discrete values of an ideal sinusoidal waveform using commonly known fitting processes.

Then, in a process further referred to as direct correlation, the digitized and optionally fitted samples of the response signal and the excitation signal are correlated.

A more detailed description of the embodiment is given below with FIG. 8.

Figure 9:
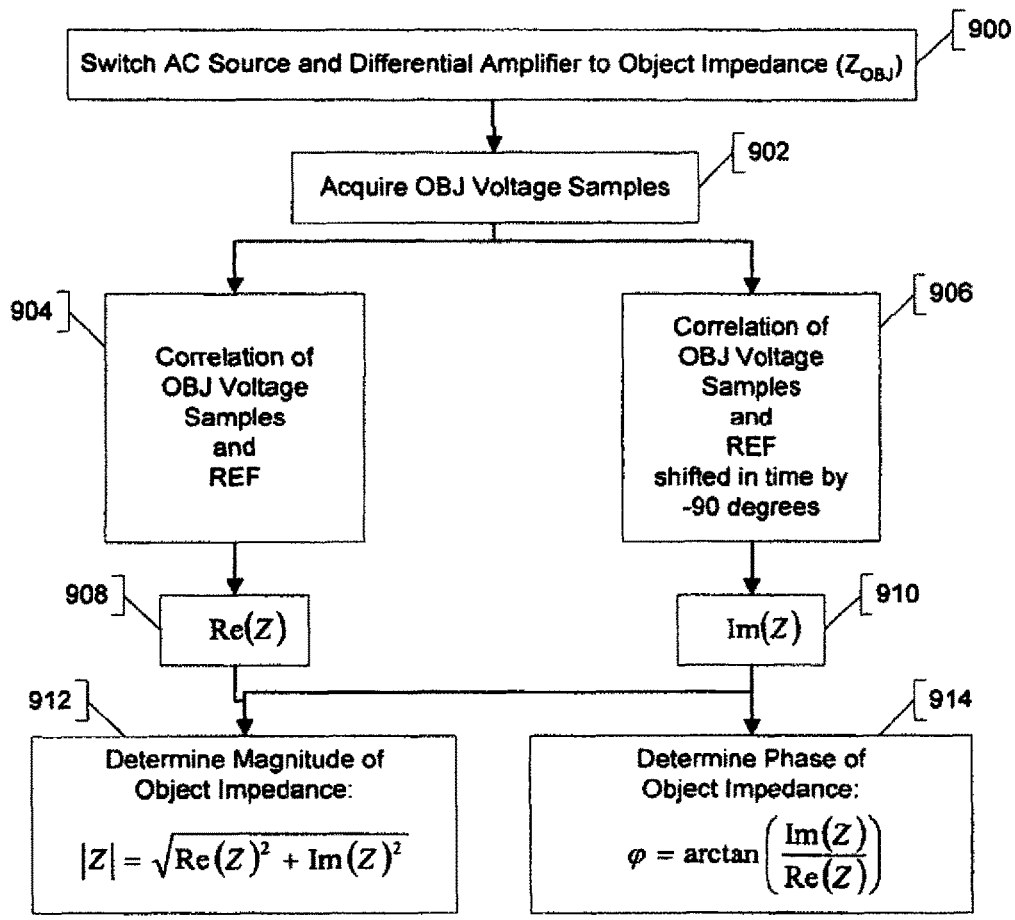
FIG. 9 is a flowchart of a sixth embodiment for the determination of the complex object impedance (Z), i.e., the impedance of interest, with the measurement of the alternating voltage but without the measurement of the alternating current (AC) applied and without the use of any calibration impedance.

According to a sixth embodiment, FIG. 9, the voltage controlled current source (VCCS) 42, which generates a single frequency (SF) or multi-frequency (MF) alternating current (AC), the excitation signal, and the differential amplifier (A) 50 are switched to the object 10 but only the resulting voltage, the response signal, is measured, amplified and digitized.

Because the frequency of the excitation signal and the response signal is known, the samples obtained, amplified and digitized can be fitted towards discrete values of an ideal sinusoidal waveform using commonly known fitting processes.

Then, in a process referred to as indirect correlation, for each frequency $f_{AC}$ of the alternating current (AC) applied, the amplified, digitized and optionally fitted samples obtained from the voltage measurement are correlated with the discrete values of an ideal sine waveform (SF), or waveforms (MF), which represent the alternating current (AC) applied in frequency $f_{AC}$, amplitude and phase.

A more detailed description is given below with FIG. 9.

Now the six possible embodiments of the invention outlined by the above overview of FIG. 3 are described in more detail.

The flowchart of FIGS. 4a and 4b describes the determination of the complex object bioimpedance ($Z_{OBJ}$), i.e., the impedance of interest, by measurements of the excitation signal, for example, an alternating current (AC) applied, and the response signal, in this example, a resulting alternating voltage, indirect correlation thereof, and the use of a calibration impedance. The description encompasses an embodiment of an alternating current (AC) of a single frequency (SF) and an ohmic resistor as the calibration impedance, but is not limited to it.

Measurement of the Calibration Impedance

FIG. 4a illustrates that, for example, by means 400 an alternating current (AC) source, including a current monitor 44, and a differential amplifier 50 are switched to the calibration impedance 20 ($Z_{CAL}$). The current monitor provides a voltage directly proportional and in phase with the alternating current (AC) applied, which is sensed, amplified and digitized by a second analog-to-digital converter (ADC 2) 46. Because the frequency of the alternating current (AC) is known a priori, the digitized samples can be fitted towards discrete values of an ideal sinusoid using commonly known algorithms and are further referred to as the Calibration Current Samples 402. The differential amplifier senses the voltage across the calibration impedance, which is amplified and, simultaneously with the second analog-to-digital converter (ADC 2) 46, digitized by a first analog-to-digital converter (ADC 1) 52. Because the frequency of the alternating current (AC) and, thus, of the voltage measured is known a priori, the digitized samples can be fitted towards discrete values of an ideal sinusoid using commonly known algorithms and are further referred to as Calibration Voltage Samples 404.

Correlation 406, i.e. pair-wise multiplication of Calibration Current Samples with the corresponding discrete values of a unity sine waveform (SIN), and accumulation, results in a value proportional as the in-phase portion of the current ($I_{AC\ CAL}'$) 414, which, at this point, is uncorrected for any phase shift caused by the measurement system. Correlation, i.e. pair-wise multiplication of Calibration Current Samples with the corresponding discrete values of a unity cosine waveform (COS), and accumulation 408, results in a value proportional to the quadrature portion of the current ($Q_{AC\ CAL}'$) 416, which, at this point, is uncorrected for any phase shift caused by the measurement system. Preferably, the unity sine waveform SIN is in phase with the sinusoidal voltage signal controlling the current source (VCCS 42, FIG. 1a).

The equivalent of the magnitude of current through the calibration impedance, $|AC_{CAL}'|$, 422, is calculated as the square root of the sum of squared in-phase portion ($I_{AC\ CAL}'$) and squared quadrature portion of current ($Q_{AC\ CAL}'$).

The phase shift of the current $\phi_{AC\ CAL}'$ 430, including any phase shift caused by the measurement system, is calculated as the arctan of the ratio of the quadrature portion ($Q_{AC\ CAL}'$) over the in-phase portion of the current ($I_{AC\ CAL}'$).

Correlation 410, i.e. pair-wise multiplication of Calibration Voltage Samples with the corresponding discrete values of a unity sine waveform (SIN), and accumulation, results in a value proportional to the in-phase portion of the voltage ($I_{V\ CAL}'$) 418, which, at this point, is uncorrected for any phase shift caused by the measurement system. Correlation, i.e. pair-wise multiplication of Calibration Voltage Samples with the corresponding discrete values of a unity cosine waveform (COS), and accumulation 412, results in a value proportional as the quadrature portion of the voltage ($Q_{V\ CAL}'$) 420, which, at this point, is uncorrected for any system phase.

The equivalent to the voltage magnitude across the calibration impedance, $|V_{CAL}'|$, 424, is calculated as the square root of the sum of squared in-phase portion ($I_{V\ CAL}'$) and squared quadrature portion of voltage ($Q_{V\ CAL}'$).

The phase shift of the voltage, $\varphi_{V\ CAL}'$, 432, including any phase shift caused by the measurement system, is calculated as the arctan of the ratio of the quadrature portion ($Q_{V\ CAL}'$) and the in-phase portion of the voltage ($I_{V\ CAL}'$).

In the preferred embodiment, however, in which an ohmic resistor (with theoretically no phase shift between current and voltage) is utilized as the calibration impedance, the aforementioned calculation reveals directly the phase shift of the system, $\varphi_{SYS}$, 434, which is determined as the difference between the phase of the voltage measured and the phase of the alternating current (AC) applied.

The equivalent to the calibration impedance magnitude, 436, is calculated as the ratio of the equivalent of the voltage magnitude equivalent across the calibration impedance, $|V_{CAL}'|$ and the magnitude of the current magnitude equivalent through the calibration impedance, $|AC_{CAL}'|$.

Measurement of the Object Impedance

Then, by means 450 the alternating current (AC) 42 source including the current monitor 44 and the differential amplifier 50 are switched to the object 10 or impedance ($Z_{OBJ}$), respectively, (FIG. 4b). The current monitor 44 provides a voltage directly proportional and in phase with the alternating current (AC) applied, which is sensed, amplified and digitized by the second analog-to-digital-converter (ADC 2) 46. Because the frequency of the alternating current (AC), the excitation signal, is known a priori, the digitized samples can be fitted towards the values of an ideal sinusoid using commonly known algorithms and are further referred to as the Object Current Samples 452. The differential amplifier senses or acquires, respectively, the voltage across the object 10, the object impedance $Z_{OBJ}$, which is amplified and, simultaneously with the second analog-to-digital converter (ADC 2) 46, digitized by the first analog-to-digital converter (ADC 1) 52. Because the frequency of the alternating current (AC), the excitation signal, and, thus, of the voltage measured, the response signal, is known, a priori, the digitized samples can be fitted towards discrete values of an ideal sinusoid using commonly known algorithms and are further referred to as Object Voltage Samples 454.

Correlation 456, i.e. pair-wise multiplication of Object Current Samples with the corresponding discrete values of a unity sine waveform (SIN), and accumulation, results in a value proportional as the in-phase portion of the current ($I_{AC\ OBJ}'$) 464, which, at this point, is uncorrected for any phase shift caused by the measurement system. Correlation 458, i.e. pair-wise multiplication of Object Current Samples with the corresponding discrete values of a unity cosine waveform (COS), and accumulation, results in a value proportional to the quadrature portion of the current ($Q_{AC\ OBJ}'$) 466, which, at this point, is uncorrected for any phase shift caused by the measurement system.

The equivalent of the object current magnitude, through the object impedance, $|AC_{OBJ}'|$, 472, is calculated as the square root of the sum of squared in-phase portion of current amplitude ($I_{AC\ OBJ}'$) and squared quadrature portion of current ($Q_{AC\ OBJ}'$).

The phase of the object current, $\varphi_{AC\ OBJ}'$, 480, including any phase shift caused by the measurement system, is calculated as the arctan of the ratio of the quadrature portion and in-phase portion of the current.

Correlation 460, i.e. pair-wise multiplication of Object Voltage Samples with the corresponding discrete values of a unity sine waveform (SIN), and accumulation, results in a value proportional to the in-phase portion of the object voltage ($I_{V\ OBJ}'$) 468, which, at this point, is uncorrected for any phase shift caused by the measurement system. Correlation 462, i.e. pair-wise multiplication of Object Voltage Samples with the corresponding discrete values of a unity cosine waveform (COS), and accumulation, results in a value proportional to the quadrature portion of the object voltage ($Q_{V\ OBJ}'$) 470, which, at this point, is uncorrected for any phase shift caused by the measurement system.

The equivalent to the voltage magnitude across the object impedance, $|V_{OBJ}'|$, 474, is calculated as the square root of the sum of the squared in-phase portion ($I_{V\ OBJ}'$) and the squared quadrature portion of voltage ($Q_{V\ OBJ}'$).

The phase of the voltage, $\varphi_{V\ OBJ}'$, 482, including any phase shift caused by the measurement system, is calculated as the arctan of the ratio of the quadrature portion ($Q_{V\ OBJ}'$) and the in-phase portion of the voltage ($I_{V\ OBJ}'$).

In the preferred embodiment, in which an ohmic resistor (with theoretically no phase shift between current and voltage) is utilized as the calibration impedance 20, the phase shift between the response signal, the voltage, measured across and the excitation signal, the alternating current (AC), applied to the object impedance, $\cos \varphi_{OBJ}$, is calculated as the difference between the phase of the voltage and the phase of the current, of which the phase shift of the system, $\varphi_{SYS}'$, 434, is subtracted by circuit 484.

The magnitude equivalent of the object impedance, $|Z_{OBJ}'|$, is calculated by circuit 486 as the ratio of the object voltage magnitude equivalent $|V_{OBJ}'|$ and the current magnitude equivalent $|AC_{OBJ}'|$, which is multiplied by the cosine of the phase shift between the voltage across and the current through the object impedance, $\cos \varphi_{OBJ}$.

The magnitude of the object impedance, $|Z_{OBJ}'|$, is calculated by circuit 488 as the ratio of the (a priori known) calibration impedance magnitude, $|Z_{CAL}|$, to the magnitude equivalent of the calibration impedance, $|Z_{CAL}'|$, times the magnitude equivalent of the object impedance, $|Z_{OBJ}'|$.

The real part (in-phase portion) of the object impedance ($Re(Z_{OBJ})$), 490, is calculated from the magnitude of the object impedance, $|Z_{OBJ}|$ and the phase of object impedance $\cos \varphi_{OBJ}$. The imaginary part (quadrature portion) of the object impedance ($Im(Z_{OBJ})$), 492, is calculated from the magnitude of object impedance, $|Z_{OBJ}'|$ and the phase of object impedance $\sin \varphi_{OBJ}$.

Alternatively, the second analog-to-digital converter (ADC 2) 46 and the first analog-to-digital converter (ADC 1) 52 can be replaced by a single analog-to-digital converter (ADC) with multiplexed inputs (not shown).

The embodiment of FIGS. 4a, 4b can be adapted for a multi-frequency (MF) alternating current (AC) application by executing the correlation processes 406, 408, 410, 412 (calibration impedance) and 456, 458, 460, 462 (object impedance) for each frequency $f_{AC}$ of the alternating current (AC) applied, then obtaining results for complex impedances depending on frequency.

The flowchart of FIG. 5 describes the determination of the complex object bioimpedance ($Z_{OBJ}$), i.e., the impedance of interest, by measurements of the excitation signal, the alternating current (AC) applied, and the response signal, the alternating voltage, direct correlation thereof, the calculation of the real and imaginary part of the object impedance, and the use of a calibration impedance. The description encompasses an embodiment of an alternating current (AC) of a single frequency (SF) and an ohmic resistor as the calibration impedance 20, but is not limited thereto.

Measurement of the Calibration Impedance

FIG. 5 illustrates that, for example, by means 500 an alternating current (AC) source, including a current monitor 44, and a differential amplifier 50 are switched to the calibration impedance 20 ($Z_{CAL}$). The current monitor 44 provides a voltage directly proportional and in phase with the alternating current (AC) applied, which is sensed, amplified and digitized by a second analog-to-digital converter (ADC 2) 46. Because the frequency of the alternating current (AC), the excitation signal, is known a priori, the digitized samples can be fitted towards discrete values of an ideal sinusoid using commonly known algorithms and are further referred to as the Calibration Current Samples 502. A differential amplifier senses the voltage across the calibration impedance, which is amplified and, synchronously with the second analog-to-digital converter (ADC 2) 46, digitized by a first analog-to-digital converter (ADC 1) 52. Because the frequency of the excitation signal and the response signal is known a priori, the digitized samples can be fitted towards discrete values of an ideal sinusoid using commonly known algorithms and are further referred to as Calibration Voltage Samples 504.

Correlation accumulation 506, i.e. pair-wise multiplication of the Calibration Voltage Samples with the corresponding Calibration Current Samples, and results in a value proportional to the real part (in-phase portion) of the calibration impedance (Re($Z_{CAL}'$)) 510, which, at this point, is uncorrected for any phase shift caused by the measurement system. Correlation 508, i.e. pair-wise multiplication of the Calibration Voltage Samples with the corresponding Calibration Current Samples, which are shifted in phase by −90 degrees, and accumulation, results in a value proportional to the imaginary part (quadrature portion) of the calibration impedance (Im($Z_{CAL}'$)) 512, which, at this point, is uncorrected for any phase shift due to the measurement system.

The calibration impedance magnitude equivalent, $|Z_{CAL}'|$, 514, is calculated as the square root of the sum of the squared real part of the calibration impedance (Re($Z_{CAL}'$)) and the squared imaginary part of the calibration impedance (Im($Z_{CAL}'$)).

The calibration impedance phase, $\varphi_{CAL}$, 516, including any phase shift due to the measurement system, is calculated as the arctan of the ratio of the imaginary part and the real part. In the preferred embodiment, however, in which an ohmic resistor (with theoretically no phase shift between the voltage across and the current through it) is utilized as the calibration impedance, the aforementioned calculation provides directly the phase shift of the system.

Measurement of the Object Impedance

Thereafter, by means 520 the alternating current (AC) source, including a current monitor 44, and the differential amplifier 50 are switched to the object 10 or object impedance ($Z_{OBJ}$). The current monitor 44 provides a voltage directly proportional and in phase with the alternating current (AC), the excitation signal, applied, which is acquired (sensed), amplified and digitized by the second analog-to-digital converter (ADC 2) 46. Because the frequency of the alternating current (ADC) is known a priori, the digitized samples can be fitted towards discrete values of an ideal sinusoid using commonly known algorithms and are further referred to as the Object Current Samples 522. The differential amplifier senses the voltage across the object impedance, the response signal, which is amplified and, simultaneously with the second analog-to-digital converter (ADC 2) 46, digitized by a first analog-to-digital converter (ADC 1) 52. Because the frequency of the alternating current (AC), the excitation signal, and, thus, of the voltage measured, the response signal, is known a priori, the digitized samples can be fitted towards discrete values of an ideal sinusoid and are further referred to as Object Voltage Samples 524.

Correlation 526, i.e. pair-wise multiplication of the Object Voltage Samples with the corresponding Object Current Samples, and accumulation, results in a value proportional to the real part (in-phase portion) of the object impedance (Re($Z_{OBJ}'$)) 530, which, at this point, is uncorrected for any phase shift caused by the measurement system. Correlation 528, i.e. pair-wise multiplication of the Object Voltage Samples with the corresponding Object Current Samples, which are shifted in time by −90 degrees, and accumulation, results in a value proportional to the imaginary part (quadrature portion) of the object impedance (Im($Z_{OBJ}'$)) 532, which, at this point, is uncorrected for any phase shift caused by the measurement system.

The object impedance magnitude equivalent, $|Z_{OBJ}'|$, 534, is calculated as the square root of the sum of the squared real part of object impedance (Re($Z_{OBJ}'$)) and the squared imaginary part of object impedance (Im($Z_{OBJ}'$)).

The object impedance phase, $\varphi_{OBJ}'$, 536, including any phase shift caused by the measurement system, further referred to as the uncorrected phase, is calculated as the arctan of the ratio of the imaginary part and the real part.

In the preferred embodiment, in which an ohmic resistor (with theoretically no phase shift) is utilized as the calibration impedance 20, the phase of the object impedance, $\varphi_{OBJ}$, 540 is calculated as the difference between the previously determined uncorrected phase, $\varphi_{OBJ}'$, and the phase of the calibration impedance, $\varphi_{CAL}$, i.e., the phase shift cause by the measurement system.

The magnitude of the object impedance 542, $|Z_{OBJ}'|$, is calculated as the ratio of the (a priori known) calibration impedance magnitude, $|Z_{CAL}'|$, to the magnitude equivalent of the calibration impedance, $|Z_{CAL}'|$, times the magnitude equivalent of the object impedance, $|Z_{OBJ}'|$.

The real part of object impedance (Re($Z_{OBJ}$)), 544, is calculated from the magnitude and phase of object impedance. The imaginary part of object impedance (Im($Z_{OBJ}$)), 546, is calculated from the magnitude and phase of object impedance.

Alternatively, the first analog-to-digital converter (ADC 1) 52 and the second analog-to-digital converter (ADC 2) 46 can be replaced by a single analog-to-digital converter (ADC) with multiplexed inputs (not shown).

The flowchart of FIG. 6 describes the determination of the complex object bioimpedance ($Z_{OBJ}$), i.e., the impedance of interest, by the application of an alternating current (AC) of which the amplitude is not measured but held constant, measurement of the voltage due to the alternating current (AC) applied, correlation thereof and use of a calibration impedance. The description encompasses the embodiment of an alternating current (AC) of a single frequency (SF) and an ohmic resistor as the calibration impedance 20, but is not limited to.

By means 600 the alternating current (AC) source, including a current monitor, and a differential amplifier 50 are switched to the calibration impedance 20, ($Z_{CAL}$). The differential amplifier acquires/senses 602 the voltage, the response signal, across the calibration impedance 20, which is amplified and digitized by a first analog-to-digital converter (ADC 1) 52. Because the frequency of the exciting signal, the alternating current (AC), and, thus, of the response signal, the voltage measured, is known a priori, the digitized samples can be fitted towards discrete values of an ideal sinusoid using commonly known algorithms and are further referred to as Calibration Voltage Samples.

Correlation 604, i.e. pair-wise multiplication of Calibration Voltage Samples with the corresponding discrete values of a unity sine waveform (SIN), and accumulation, results in a value proportional to the real part (in-phase portion) of the calibration impedance 608, which, at this point, is uncorrected for any phase shift caused by the measurement system. Correlation 606, i.e. pair-wise multiplication of Calibration Voltage Samples with the corresponding discrete values of a unity cosine waveform (COS), and accumulation, results in a value proportional to the imaginary part (quadrature portion) of the calibration impedance 610, which, at this point, is uncorrected for any phase shift caused by the measurement system.

The magnitude of an equivalent to the calibration impedance 612 is calculated as the square root of the sum of the squared uncorrected real part (in-phase portion) of the calibration impedance ($Re(Z_{OBJ}')$) 608 and the squared uncorrected imaginary part (quadrature portion) of the calibration impedance ($Im(Z_{OBJ}')$) 610.

The phase of the calibration impedance, $\varphi_{CAL}$, 614, including any phase shift caused by the measurement system, is calculated as the arctan of the ratio of the imaginary part and the real part of calibration impedance. In the preferred embodiment, however, in which an ohmic resistor (with theoretically no phase) is utilized as the calibration impedance, the aforementioned calculation provides directly the phase shift of the measurement system.

Then, by means 620 the alternating current (AC) source, including a current monitor 44, and the differential amplifier 50 are switched to the object 10, the impedance ($Z_{OBJ}$). The differential amplifier acquires/senses 622 the voltage, the response signal, across the object impedance 20, which is amplified and digitized by a first analog-to-digital converter (ADC 1) 52. Because the frequency of the excitation signal, the alternating current (AC), and, thus, of the response signal, the voltage measured, is known a priori, the digitized samples can be fitted towards discrete values of an ideal sinusoid using commonly known algorithms and are further referred to as Object Voltage Samples. Correlation 624, i.e. pair-wise multiplication of Object Voltage Samples with the corresponding discrete values of a unity sine waveform (SIN), and accumulation, results in a value proportional to the real part (in-phase portion) of the object impedance ($Re(Z_{OBJ}')$) 628, which, at this point, is uncorrected for any phase shift caused by the measurement system. Correlation 626, i.e. pair-wise multiplication of Object Voltage Samples with the corresponding discrete values of a unity cosine waveform (COS), and accumulation, results in a value proportional to the imaginary part (quadrature portion) of the object impedance ($Im(Z_{OBJ}')$) 630, which, at this point, is uncorrected for any phase shift caused by the measurement system.

The equivalent to the magnitude of object impedance $|Z_{OBJ}'|$, 632, is calculated as the square root of the sum of the squared uncorrected real part (in-phase portion) of the object impedance ($Re(Z_{OBJ}')$) 628 and the squared imaginary part (quadrature portion) of the object impedance ($Im(Z_{OBJ}')$) 630.

The phase of the object impedance, $\varphi_{OBJ}'$, 634, including any phase shift due to the measurement system, is calculated as the arctan of the ratio of the imaginary part over real part of the (uncorrected) object impedance.

In the preferred embodiment, in which an ohmic resistor (with theoretically no phase shift between the voltage across and the current trough it) is utilized as the calibration impedance 20, the phase of the object impedance, $\varphi_{OBJ}$, 640, is calculated to the difference of previously determined uncorrected object phase, $\varphi_{OBJ}'$, and calibration impedance phase, i.e., the phase shift caused by the measurement system.

The magnitude of the object impedance, $|Z_{OBJ}'|$, 642, is calculated as the ratio of the (a priori known) calibration impedance magnitude, $|Z_{CAL}'|$, and the calibration impedance magnitude equivalent, $|Z_{CAL}'|$, times the magnitude equivalent of the object impedance, $|Z_{OBJ}'|$.

The real part (in-phase portion) of the object impedance ($Re(Z_{OBJ})$) is calculated from the magnitude and phase of object impedance by means 644. The imaginary part (quadrature portion) of the object impedance ($Im(Z_{OBJ})$) is calculated from the magnitude and phase shifted by −90 degrees of object impedance by means 646.

Alternatively, the embodiment of FIG. 6 can be adapted for a multi-frequency (MF) alternating current (AC) application by executing the correlation processes 604, 606 (calibration impedance) and 624, 626 (object impedance) for each frequency $f_{AC}$ of the alternating current (AC) applied, then obtaining results for complex impedances depending on frequency.

The flowchart of FIG. 7 describes the determination of the complex object bioimpedance (Z), i.e., the impedance of interest, by measurements of the alternating current (AC) of a single frequency (SF) and the alternating voltage, indirect correlation thereof, and without the use of any calibration impedance.

By means 700 an alternating current (AC) source, including a current monitor 44, and a differential amplifier 50 are connected to the object 10, the object impedance ($Z_{OBJ}$). The current monitor 44 provides a voltage directly proportional and in phase with the alternating current (AC), the excitation signal, applied, which is sensed, amplified and digitized by a second analog-to-digital converter (ADC 2) 46. Because the frequency of the excitation signal, the alternating current (AC), is known a priori, the digitized samples can be fitted towards discrete values of an ideal sinusoid using commonly known algorithms and are further referred to as the Object Current Samples 702. Each Object Current Sample equates to an instantaneous value of the current signal. The differential amplifier 50 senses the response signal, the voltage across the object impedance, which is amplified and, simultaneously with the second analog-to-digital converter (ADC 2) 46, digitized by a first analog-to-digital converter (ADC 1) 52. Because the frequency of the excitation signal, the alternating current (AC), is known a priori, the digitized samples can be fitted towards discrete values of an ideal sinusoid using commonly known algorithms and are further referred to as Object Voltage Samples. Each Object Voltage Sample 704 equates to an instantaneous value of the voltage signal. Correlation 706, i.e. pair-wise multiplication of Object Current Samples with the corresponding discrete values of a unity sine waveform (SIN), and accumulation, results in a value equal to the in-phase portion of the current ($I_{AC}$) 714, which, at this point, is uncorrected for any phase shift caused by the measurement system. Correlation 708, i.e. pair-wise multiplication of Current Samples (OBJ) with the corresponding discrete values of a unity cosine waveform (COS), and accumulation, results in a value equal to the quadrature portion of the current ($Q_{AC}$) 716, which, at this point, is uncorrected for any phase shift due to the measurement system.

The current magnitude through the object impedance, $|AC|$, 722, is calculated as the square root of the sum of squared in-phase portion of current amplitude ($I_{AC}$) and squared quadrature portion of current ($Q_{AC}$).

The phase of the current, $\varphi_{AC}$, 730, including any phase shift due to the measurement system, is calculated as the arctan of the ratio of the quadrature portion and the in-phase portion of the current.

Correlation 710, i.e. pair-wise multiplication of Object Voltage Samples with the corresponding discrete values of a unity sine waveform (SIN), and accumulation, results in a value equal to the in-phase portion of the voltage ($I_V$) 718, which, at this point, is uncorrected for any phase shift caused by the measurement system. Correlation 712, i.e. pair-wise multiplication of Object Voltage Samples with the corresponding discrete digital samples of a unity cosine waveform (COS), and accumulation, results in a value equal to the quadrature portion of the voltage ($Q_V$)) 720, which, at this point, is uncorrected for any phase shift caused by the measurement system.

The voltage magnitude across the calibration impedance, |V|, 724, is calculated as the square root of the sum of the squared in-phase portion ($I_V$)) and the squared quadrature portion of voltage ($Q_V$).

The phase of the voltage, $\varphi_V$, 732, including any phase shift caused by the measurement system, is calculated as the arctan of the ratio of the quadrature portion ($Q_V$)) and the in-phase portion of the voltage ($I_V$).

In the preferred embodiment, in which an ohmic resistor (with theoretically no phase shift between current and voltage) is utilized as the calibration impedance 20, the phase shift $\varphi$, 724, of the impedance is calculated as the difference between the phase of the voltage and the phase of the current.

The magnitude of the object impedance, |Z|, 736, is calculated as the ratio of the object voltage magnitude |V| and the current magnitude.

The real part (in-phase portion) of the object impedance (Re(Z)), 738, is calculated from the magnitude and phase of object impedance. The imaginary part (quadrature portion) of the object impedance (Im(Z)), 740, is calculated from the magnitude and the phase shifted by −90 degrees of object impedance.

Alternatively, the first analog-to-digital converter (ADC 1) 52 and the second analog-to-digital converter (ADC 2) 46 can be replaced by a single analog-to-digital converter (ADC) with multiplexed inputs (not shown).

The embodiment of FIG. 7 can be adapted for a multi-frequency (MF) alternating current (AC) application by executing the correlation processes 706, 708, 710, 712 for each frequency $f_{AC}$ of the alternating current (AC) applied, then obtaining results for complex impedances depending on frequency.

The flowchart of FIG. 8 describes the determination of the complex object bioimpedance (Z), i.e., the impedance of interest, by measurements of the alternating current (AC) and the alternating voltage, direct correlation thereof, and without the use of any calibration impedance.

By means 800 an alternating current (AC) source, including a current monitor 44, and a differential amplifier 50 are connected to the object 10, the object impedance ($Z_{OBJ}$). The current monitor 44 provides a voltage directly proportional and in phase with the excitation signal, the alternating current (AC) applied, which is sensed, amplified and digitized by a second analog-to-digital converter (ADC 2) 46. Because the frequency of the excitation signal, the alternating current (AC), is known a priori, the digitized samples can be fitted towards discrete values of an ideal sinusoid using commonly known algorithms and are further referred to as the Object Current Samples. Each Object Current Sample 802 equates to an instantaneous value of the current signal. The differential amplifier 50 senses the response signal, the voltage across the object impedance, which is amplified and, simultaneously with the second analog-to-digital converter (ADC 2) 46, digitized by a first analog-to-digital converter (ADC 1) 52. Because the frequency of the excitation signal, the alternating current (AC), and, thus, of the response signal, the voltage measured, is known a priori, the digitized samples can be fitted towards discrete values of an ideal sinusoid using commonly known algorithms and are further referred to as Object Voltage Samples. Each Object Voltage Sample 804 equates to an instantaneous value of the voltage signal.

Correlation 806, i.e. pair-wise multiplication of Object Voltage Samples with the corresponding discrete values of the Object Current Samples, and accumulation, results in a value equal to the real part (in-phase portion) of the impedance (Re(Z)) 810.

Correlation 808, i.e. pair-wise multiplication of Object Voltage Samples with the corresponding discrete digital samples of the Object Current Samples, which are shifted in phase by −90 degrees, and accumulation, results in a value equal to the imaginary part (quadrature portion) of the impedance (Im(Z)) 812.

The magnitude of the object impedance, |Z|, 814, is calculated as the square root of the sum of the squared real part (Re(Z)) and the squared imaginary part of the impedance (Im(Z)).

The phase of the object impedance, $\varphi_{AC}$, 816, including any phase shift caused by the measurement system, is calculated as the arctan of the ratio of the imaginary part and the real part of the impedance. In addition, the system-related phase shift may be compensated for in a phase shift applied to either the Current or Voltage Samples (not shown).

Alternatively, the first analog-to-digital converter (ADC) 52 and the second analog-to-digital converter (ADC) 46 can be replaced by a single analog-to-digital converter (ADC) with multiplexed inputs (not shown).

The flowchart of FIG. 9 describes the determination of the complex object bioimpedance (Z), i.e., the impedance of interest, by the application of an alternating current (AC) of which the amplitude is not measured but known and held constant, measurement of the alternating voltage due to the alternating current (AC) application, and without the use of any calibration impedance.

By means 900 the alternating current (AC) source, including a current monitor 44, and a differential amplifier 50 are connected to the object 10, the object impedance (Z). The differential amplifier senses the response signal, the voltage across the object impedance, which is amplified, sampled and digitized by a first analog-to-digital converter (ADC) 52. Because the frequency of the excitation signal, the alternating current (AC), and, thus, of the response signal, the voltage measured, is known a priori, the digitized samples can be fitted towards the discrete values of an ideal sinusoid using commonly known algorithms and are further referred to as Object Voltage Samples. Each Object Voltage Sample 902 equates to an instantaneous value of the voltage signal.

Correlation 904, i.e. pair-wise multiplication of the Object Voltage Samples with the corresponding discrete, a priori calibrated, Reference Current Samples (REF), and accumulation, results in a value equal to the real part (in-phase portion) of the impedance (Re(Z)) 908.

Correlation 906, i.e. pair-wise multiplication of Object Voltage Samples with the corresponding discrete, a priori calibrated, Reference Current Samples (REF), which are shifted in phase by −90 degrees, and accumulation, results in a value equal to the imaginary part (quadrature portion) of the impedance (Im(Z)) 910.

The magnitude of the object impedance, |Z|, 912, is calculated as the square root of the sum of the squared real part (Re(Z)) and the squared imaginary part of the impedance (Im(Z)).

The phase of the object impedance, φ, 914, including any phase shift due to the measurement system, is calculated as the arctan of the ratio of the imaginary part and the real part of the impedance. In addition, the system-related phase shift may be compensated for a phase shift applied to the Reference Current Samples (REF) (not shown).

The embodiment of FIG. 9 can be adapted for a multi-frequency (MF) alternating current (AC) application by executing the correlation processes 904, 906 for each frequency $f_{AC}$ of the alternating current (AC) applied, then obtaining results for complex impedances depending on frequency.

The following entries illustrate some examples of the invention:

Entry 1. Method for digital demodulation and further processing of signals obtained in the measurement of complex electrical bioimpedance or bioadmittance in a biological object due to biological activity, in particular in the measurement of the change and/or rate of change in electrical bioimpedance or bioadmittance, by
generating an excitation signal of known frequency content, applying said excitation signal to the object by a first pair of electrodes,
sensing the response signal of the object by a second pair of electrodes,
sampling and digitizing said response signal to acquire a digitized response signal representing the response signal with respect to frequency content, amplitude and phase,
correlating for each frequency $f_{AC}$ of the excitation signal applied digitized samples of said digitized response signal with the discrete values of a sinusoidal reference signal to the excitation signal (indirect correlation) or of said excitation signal (direct correlation), respectively, and
calculating, using said correlated signals for each frequency $f_{AC}$ of the excitation signal applied, complex values for the bioimpedance $Z(f_{AC})$, or the bioadmittance $Y(f_{AC})$, respectively, and providing, over time, a set of digital bioimpedance waveforms $Z(f_{AC},t)$, or digital bioadmittance waveforms $Y(f_{AC},t)$, either
separating the base bioimpedance $Z_0(f_{AC})$, or base bioadmittance $Y_0(f_{AC})$, from said waveforms,
separating the changes of bioimpedance $\Delta Z(f_{AC},t)$, or the changes of bioadmittance $\Delta Y(f_{AC},t)$ from said waveforms, and
determining the rate of change of the changes in bioimpedance $d(\Delta Z(f_{AC},t))/dt$,
or the rate of change of the changes in bioadmittance $d(\Delta Y(f_{AC},t))/dt$,
or
determining the rate of change in the bioimpedance waveforms $dZ(f_{AC},t)/dt$, or the rate of the change in the bioadmittance waveforms $dY(f_{AC},t)/dt$, and finally
recording the temporal course of said base bioimpedance or bioadmittance and of said changes or said rate of change in bioimpedance or bioadmittance.

Entry 2. Method according to entry 1, wherein the excitation signal is a sinusoidal signal of a known single frequency $f_{AC}$.

Entry 3. Method according to entry 1 or 2, wherein the excitation signal has an amplitude and phase which are substantially constant over time.

Entry 4. Method according to any of entries 1 to 3, wherein the excitation signal is switched either to the object or to a calibration impedance, preferably an ohmic resistor.

Entry 5. Method according to any of entries 1 to 4, wherein the excitation signal is generated by the use of discrete values of a sinusoidal waveform, or of a number of sinusoidal waveforms, stored in an addressable sine look-up table which are converted into analog excitation signals of the desired frequency content, amplitude and phase.

Entry 6. Method according to any of entries 1 to 5, wherein the excitation signal is generated by time-controlled direct digital synthesizing (DDS) and in turn driving an excitation source generating the excitation signals of the desired frequency content, amplitude and phase.

Entry 7. Method according to any of entries 1 to 6 wherein the excitation signal contains frequencies in the range of 1 kHz to 1 MHz, preferably about 10 kHz to 200 kHz.

Entry 8. Method according to entry 3, wherein the excitation signal has amplitudes of the alternating current (AC) in the range of 0.01 mA to 5 mA.

Entry 9. Method according to any of entries 1 to 8, wherein the response signal is sampled by a first fast analog-to-digital converter (ADC) at a rate significantly higher than the highest frequency of the excitation signal, preferably by a factor in the range of 4 to 20, in particular about 10.

Entry 10. Method according to any of entries 1 to 9 wherein the excitation signal or the signal representing the excitation signal is sampled by a second fast analog-to-digital converter (ADC) at a rate significantly higher than the highest frequency of the excitation signal, preferably by a factor in the range of 4 to 20, in particular about 10.

Entry 11. Method according to any of entries 1 to 10, wherein, for each frequency $f_{AC}$ of the excitation signal applied, the results of the correlation processes form digital waveforms $Z(f_{AC},t)$, which are either input to a low pass filter for obtaining the base impedance $Z_0(f_{AC})$, or base admittance $Y_0(f_{AC})$ of the object, input to a high pass filter for obtaining a waveform representing the changes in bioimpedance $\Delta Z(f_{AC},t)$, or bioadmittance $\Delta Y(f_{AC},t)$ of the object, respectively, and optionally input to a differentiator for obtaining the rate of change of the changes in bioimpedance $d(\Delta Z(f_{AC},t))/dt$, or the rate of change of the changes in bioadmittance $d(\Delta Y(f_{AC},t))/dt$, or input to a differentiator for obtaining the rate of change in the bioimpedance waveforms $dZ(f_{AC},t)/dt$, or the rate of the change in the bioadmittance waveforms $dY(f_{AC},t)/dt$.

Entry 12. Method according to any of entries 1 to 11, wherein separate correlation processes are used to determine the in-phase portion $Re(Z(f_{AC},t))$ and the quadrature portion $Im(Z(f_{AC},t))$ of the bioimpedance of the object, or the in-phase portion $Re(Y(f_{AC},t))$ and the quadrature portion $Im(Y(f_{AC},t))$ of the bioadmittance of the object, respectively.

Entry 13. Method according to entry 4, comprising:
applying the excitation signal to the calibration impedance,
measuring, sampling and digitizing the excitation signal or a signal representing the excitation signal to acquire Excitation Signal Samples,
measuring, sampling and digitizing the response signal across the calibration impedance to acquire Response Signal Samples, for each frequency $f_{AC}$ of the excitation signal applied,
correlating the Excitation Signal Samples with discrete values of an ideal sine waveform in order to obtain a value proportional to the in-phase portion of the excitation signal related to the ideal sine waveform as reference sine,
correlating the Excitation Signal Samples with discrete values of an ideal cosine waveform in order to obtain a value proportional to the quadrature portion of the excitation signal,
correlating the Response Signal Samples with discrete values of an ideal sine waveform in order to obtain a value proportional to the in-phase portion of the response signal,
correlating the Response Signal Samples with discrete values of an ideal cosine waveform in order to obtain a value proportional to the quadrature portion of the response signal,
calculating an equivalent for the magnitude and a phase of the excitation signal,
calculating an equivalent for the magnitude and a phase of the response signal,
calculating an equivalent for the magnitude of the calibration impedance,
calculating a system phase,
thereafter applying the excitation signal to the object,
measuring, sampling and digitizing the excitation signal or a signal representing the excitation signal to acquire the Excitation Signal Samples,
measuring, sampling and digitizing the response signal across the bioimpedance of the object, with the samples obtained further referred to as the Response Signal Samples,
for each frequency $f_{AC}$ of the excitation signal applied,
correlating the Excitation Signal Samples with discrete values of an ideal sine waveform in order to obtain a value proportional to the in-phase portion of the excitation signal related to the reference sine,
correlating the Excitation Signal Samples with discrete values of an ideal cosine waveform in order to obtain a value proportional to the quadrature portion of the excitation signal,
correlating the Response Signal Samples with discrete values of an ideal sine waveform in order to obtain a value proportional to the in-phase portion of the response signal,
correlating the Response Signal Samples with discrete values of an ideal cosine waveform in order to obtain a value proportional to the quadrature portion of the response signal,
calculating an equivalent for the magnitude and a phase of the excitation signal,
calculating an equivalent for the magnitude and a phase of the response signal,
calculating an equivalent for the magnitude and a phase of the bioimpedance of the object,
calculating the magnitude of the bioimpedance $Z(f_{AC},t)$ of the object,
calculating the in-phase portion $Re(Z(f_{AC},t))$ and the quadrature portion $Im(Z(f_{AC},t))$ of the bioimpedance of the object,
or the in-phase portion $Re(Y(f_{AC},t))$ and the quadrature portion $Im(Y(f_{AC},t))$ of the admittance of the object.
(FIG. 4)

Entry 14. Method according to any of entries 1 to 13, wherein a cross-correlation signal is calculated as a function of a time delay τ between the excitation signal and the response signal by correlating the excitation signal with the response signal after delay of the response signal by the time delay τ with respect to the excitation signal.

Entry 15. Method according to entry 14, wherein the complex Fourier transform of the cross-correlation signal is calculated to obtain complex values proportional to the complex bioimpedance.

Entry 16. Apparatus for digital demodulation and further processing of signals obtained by testing means in the measurement of electrical bioimpedance or bioadmittance in a biological object, in particular in the measurement of the change and/or rate of change in electrical bioimpedance or bioadmittance, the testing means comprising:
signal generating means (42, 44) generating an excitation signal of known frequency content,
a first pair of electrodes (12, 14) for applying said excitation signal to the object,
a second pair of electrodes (16, 18) for sensing the response signal across the object due to the application of said excitation signal,
first measuring means (50, 52) for acquiring, sampling and digitizing said response signal to obtain a digitized response signal representing the response signal with respect to frequency content, amplitude and phase,
optional second measuring means (44, 46) for acquiring, sampling and digitizing said excitation signal to obtain a digitized excitation signal representing said excitation signal with respect to frequency content, amplitude and phase,
memory means (48, 58) for temporarily storing said digitized response signal and optionally said digitized excitation signal,
digital demodulation means (80; 81-86) for correlating for each frequency $f_{AC}$ of the excitation signal applied digitized samples of said digitized response signal with corresponding discrete values of a sinusoidal reference signal to the excitation signal (indirect correlation) or said excitation signal (direct correlation), respectively,
and
processing means (60) for calculating for each frequency $f_{AC}$ of the excitation signal applied complex values for the bioimpedance $Z(f_{AC})$, or the bioadmittance $Y(f_{AC})$, respectively, from the output values of the digital demodulation means, providing, over time, a set of digital bioimpedance waveforms $Z(f_{AC},t)$, or a set of digital bioadmittance waveforms $Y(f_{AC},t)$, either a first separating means (64) adapted to separate the base impedance $Z_0(f_{AC})$, or base admittance $Y_0(f_{AC})$, from said waveforms,
a second separating means (66) adapted to separate the changes in the bioimpedance $\Delta Z(f_{AC},t)$, or the changes in the bioadmittance $\Delta Y(f_{AC},t)$ from said waveforms, and
a differentiating means (67) for obtaining the rate of change of the changes in bioimpedance $d(\Delta Z(f_{AC},t))/dt$ or rate of change of the changes in bioadmittance $d(\Delta Y(f_{AC},t))/dt$, respectively,
or a differentiating means (67) means for obtaining the rate of change in the bioimpedance waveforms $dZ(f_{AC},t)/dt$, or the rate of the change in the bioadmittance waveforms $dY(f_{AC},t)/dt$, and
recording means (110) for either recording the temporal course of said base bioimpedance or bioadmittance and of said changes in bioimpedance or bioadmittance or recording the rate of change in bioimpedance or bioadmittance waveforms.

Entry 17. Apparatus according to entry 16, wherein the signal generating means (42, 44) is adapted to generate a sinusoidal excitation signal of a known single frequency $f_{AC}$.

Entry 18. Apparatus of entry 16 or 17 comprising a calibration impedance (20), especially an ohmic resistor, and switching means (30, 32, 34, 36) for switching the signal generating means (42, 44) and first measuring means (50, 52) either to the object (10) or to the calibration impedance (20).

Entry 19. Apparatus of any of entries 16 to 18 wherein the signal generating means (42, 44) is adapted to generate the excitation signal by use of discrete values of a sinusoidal waveform, or by superposition of a number of sinusoidal waveforms, stored in an addressable sine look-up table (70) and to transform said waveforms onto a digital-analog-converter DAC (40) connected to a voltage controlled current source (42) of the signal generating means.

Entry 20. Apparatus of any of entries 16 to 19, wherein a second fast analog-to-digital converter (46) is adapted to sample the excitation signal or the signal representing the excitation signal at a rate significantly higher than the highest frequency of the excitation signal, preferably by a factor in the range of 4 to 20, in particular about 10.

Entry 21. Apparatus of any of entries 16 to 20 comprising a direct digital synthesizer (DDS) for the generation of a sinusoidal waveform, or for superposition of a number of sinusoidal waveforms.

Entry 22. Apparatus according to entry 16 or 18 wherein the signal generating means (42, 44) is adapted to generate a sinusoidal excitation signal of frequencies in the range of 1 kHz to 1 MHz.

Entry 23. Apparatus according to entry 22 wherein the signal generating means (42, 44) is adapted to generate an excitation alternating current (AC) of amplitudes in the range of 0.01 mA to 5 mA.

Entry 24. Apparatus according to any of entries 16 to 23 comprising demodulator means (80; 81-86) for digitally demodulating, for each frequency $f_{AC}$ of the alternating current (AC) applied, the response signal, which is sampled and digitized by the first analog-to-digital converter (52), by correlation over a number of cycles, the cycle length being defined by the frequency $f_{AC}$ of the alternating current (AC) applied, of the digitized voltage signal with a digitized signal representing the frequency-related portion of the alternating current (AC) applied, the multiplication and accumulation of this demodulation is performable by a multiplier/accumulator (MACC) controlled by the timing control (62) multiplying pairs of digitized voltage samples and digitized values representing the alternating current, the latter ones taken from a sine table (70; 71-73), and accumulating the products.

Entry 25. Apparatus of entry 16 and 24 comprising separate correlation means (81-86) for determining, for each frequency $f_{AC}$ of the alternating current (AC) applied, the in-phase portion $Re(Z(f_{AC},t))$ of the bioimpedance $Z(f_{AC},t)$ or $Re(Y(f_{AC},t))$ of the bioadmittance $Y(f_{AC},t)$, respectively, and the quadrature portion $Im(Z(f_{AC},t))$ or $Im(Y(f_{AC},t))$, respectively.

Entry 26. Apparatus according to any of entries 23 to 25 wherein the output of the digital demodulator means (80; 81-86) forms a digital waveform which is input either to a first filter set (64) adapted to separate the base impedance $Z_0(f_{AC})$, or base admittance $Y_0(f_{AC})$, from said waveforms, a second filter set (66) adapted to separate the changes in the bioimpedance $\Delta Z(f_{AC},t)$, or the changes in the bioadmittance $\Delta Y(f_{AC},t)$ from said waveforms, and a differentiator (67) for obtaining the rate of change of the changes in bioimpedance $d(\Delta Z(f_{AC},t))/dt$ or rate of change of the changes in bioadmittance $d(\Delta Y(f_{AC},t))/dt$, respectively, or a differentiator (67) for obtaining the rate of change in the bioimpedance waveforms $dZ(f_{AC},t)/dt$, or the rate of the change in the bioadmittance waveforms $dY(f_{AC},t)/dt$ of the object.

Entry 27. Apparatus according to any of entries 23 to 26, wherein for the calibration of the apparatus when the switching means (30, 32, 34, 36; 400) connect the alternating current (AC) source (40, 42) and the first measuring means (50, 52) to the calibration impedance (20) in order to acquire Calibration Current Samples (402) and Calibration Voltage Samples (404), for each frequency $f_{AC}$ of the alternating current (AC) applied, a correlating means (406) correlates the Calibration Current Samples (402) with the discrete values of an ideal sine waveform in order to obtain a value (414) proportional to the in-phase portion of the alternating current applied (indirect correlation), a correlation means (408) correlates the Calibration Current Samples (402) with the discrete values of an ideal cosine waveform in order to obtain a value (416) proportional to the quadrature portion of the alternating current applied, a correlation means (410) correlates the Calibration Voltage Samples (404) with the discrete values of an ideal sine waveform in order to obtain a value (418) proportional to the in-phase portion of the voltage measured, a correlation means (412) correlates the Calibration Voltage Samples (404) with the discrete values of an ideal cosine waveform in order to obtain a value (420) proportional to the quadrature portion of the voltage measured, a calculating means (422) determines an equivalent to the current magnitude from the values proportional to in-phase portion (414) and quadrature portion (416) of the current applied, a calculating means (424) determines an equivalent to the voltage magnitude from the values proportional to the in-phase portion (418) and the quadrature portion (420) of the voltage measured, a calculating means (430) determines a current phase from the values proportional to the in-phase portion (414) and the quadrature portion (416) of the current applied, a calculating means (432) to determines a voltage phase of the values proportional to in-phase portion (418) and quadrature portion (420) of the voltage measured, a calculating means (434) determines a system phase (440) as the difference between the voltage phase (432) and the current phase (430) and a calculating means (436) determines an equivalent for the magnitude of the calibration impedance (442) from the ratio of the equivalent for the voltage magnitude (424) and the equivalent of the current magnitude (422), wherein further:

for the digital demodulation when the switching means (30, 32, 34, 36; 450) connect the alternating current (AC) source (70, 40, 42) and the second/first measuring means (50, 52) to the object (10) in order to acquire Object Current Samples (452) and Object Voltage Samples (454), wherein for each frequency $f_{AC}$ of the alternating current (AC) applied, a correlating means (456) correlates the Object Current Samples (452) with the discrete values of an ideal sine waveform in order to obtain a value (464) proportional to the in-phase portion of the alternating current applied (indirect correlation), a correlation means (458) correlates the Object Current Samples (452) with the discrete values of an ideal cosine waveform in order to obtain a value (466) proportional to the quadrature portion of the alternating current applied, a correlation means (460) correlates the Object Voltage Samples (454) with the discrete values of an ideal sine waveform in order to obtain a value (468) proportional to the in-phase portion of the voltage measured, a correlation means (462) correlates the Object Voltage Samples (454) with the discrete values of an ideal cosine waveform in order to obtain a value (470) proportional to the quadrature portion of the voltage measured, a calculating means (472) determines an equivalent to the current magnitude from the values proportional to in-phase portion (464) and quadrature portion (466) of the current applied, a calculating means (474) determines an equivalent to the voltage magnitude from the values proportional to the in-phase portion (468) and the quadrature portion (470) of the voltage measured, a calculating means (480) determines a current phase from the values proportional to the in-phase portion (464) and the quadrature portion (466) of the current applied, a calculating means (482) determines a voltage phase from the values proportional to in-phase portion (468) and quadrature portion (470) of the voltage measured, a calculating means (484) determines an object phase as the difference between the voltage phase (480) and the current phase (482), corrected for the system phase (440) and a calculating means (486) determines an equivalent for the magnitude of the object impedance from the ratio of the equivalent for the voltage magnitude (474) and the equivalent of the current magnitude (472)

a calculating means (488) determines the magnitude of the object impedance from the ratio of the a priori known magnitude of the calibration impedance (20) and the equivalent for the calibration impedance magnitude (442), multiplied by the equivalent for the object impedance magnitude (486), and further comprising in the event the real or imaginary portion of the object impedance is further processed:

a calculating means (490) to determines the in-phase portion (real part) and/or a calculating means (492) to calculates the quadrature portion (imaginary part) from the magnitude (488) and phase (484) of the object impedance. (FIGS. 4a,b)

Entry 28. Apparatus according to any of entries 23 to 26, wherein:

for the calibration of the apparatus when the switching means (30, 32, 34, 36; 500) connect the alternating current (AC) source (40, 42) and the first measuring means (50, 52) to the calibration impedance (20) in order to acquire Calibration Current Samples (502) and Calibration Voltage Samples (504), for the frequency $f_{AC}$ of the alternating current (AC) applied a correlating means (506) correlates the Calibration Current Samples (502) with the Calibration Voltage Samples (504) in order to obtain a value (510) proportional to the in-phase portion of the calibration impedance (direct correlation), and a correlation means (508) correlates the Calibration Current Samples (502) with the Calibration Voltage Samples (504) samples, which are shifted in time by −90 degrees, in order to obtain a value (512) proportional to the quadrature portion of the calibration impedance, a calculating means (514) calculates an equivalent to the magnitude of the calibration impedance from the in-phase portion (510) and quadrature portion (512), a calculating means (516) calculates the phase of the calibration impedance from the in-phase portion (510) and quadrature portion (512), wherein further:

for the digital demodulation when the switching means (30, 32, 34, 36; 520) connect the alternating current (AC) source (40, 42) and the first measuring means (50, 52) to the object (10) in order to acquire Object Current Samples (522) and Object Voltage Samples (524), for the frequency $f_{AC}$ of the alternating current (AC) applied a correlating means (526) correlates the Object Current Samples (522) with the Object Voltage Samples (524) in order to obtain a value (530) proportional to the in-phase portion of the calibration impedance (direct correlation), and a correlation means (528) correlates the Object Current Samples (522) with the Object Voltage Samples (524) samples, which are shifted in time by −90 degrees, in order to obtain a value (532) proportional to the quadrature portion of the calibration impedance, a calculating means (534) calculates an equivalent to the magnitude of the object impedance from the in-phase portion (530) and quadrature portion (532), a calculating means (536) calculates the uncorrected phase of the object impedance from the in-phase portion (530) and quadrature portion (532), calculating means (540) for calculating the correct phase of the object impedance from the uncorrected object impedance (536) and from the phase of the calibration impedance (516), calculating means (542) for calculating the magnitude of the object impedance from the ratio of the a priori known magnitude of the calibration impedance (20) and the determined equivalent for the calibration impedance magnitude (514), multiplied by the determined equivalent for the object impedance magnitude (534), and wherein further in the event the real or imaginary portion of the object impedance is further processed, calculating means (544) to calculate the in-phase portion (real part) and/or calculating means (546) to calculate the quadrature portion (imaginary part) from the magnitude (542) and phase (540) of the object impedance.

(FIG. 5)

Entry 29. Apparatus according to any of entries 23 to 26, wherein:

for the calibration of the apparatus when the switching means (30, 32, 34, 36; 600) connect the alternating current (AC) source (70, 40, 42) and the first measuring means (50, 52) to the calibration impedance (20) in order to acquire Calibration Voltage Samples (602), for each alternating current frequency $f_{AC}$ applied, a correlating means (604) correlates the Calibration Voltage Samples (602) with the discrete values of an ideal sine waveform in order to obtain a value (608) proportional to the in-phase portion of the calibration impedance, a correlation means (606) correlates the Calibration Voltage Samples (602) with the discrete values of an ideal cosine waveform in order to obtain a value (610) proportional to the quadrature portion of the calibration impedance, a calculation means (612) determines an equivalent to the magnitude of the calibration impedance, a calculation means (614) determines the phase of the calibration impedance, wherein further:

for the digital demodulation when the switching means (30, 32, 34, 36; 620) connect the alternating current (AC) source 70, 40, 42) and the first measuring means (50, 52) to the object (10) in order to acquire Object Voltage Samples (622), for each alternating current frequency $f_{AC}$ applied, a correlating means (624) correlates the Object Voltage Samples (622) with the samples of an ideal sine waveform in order to obtain a value (628) proportional to the in-phase portion of the object impedance, a correlation means (626) correlates the Object Voltage Samples (622) with the samples of an ideal cosine waveform in order to obtain a value (630) proportional to the quadrature portion of the object impedance, a calculation means (632) determines an equivalent to the magnitude of the object impedance, a calculation means (634) determines the phase of the uncorrected object impedance, a calculating means (640) determines the correct phase of the object impedance by subtracting the phase of the calibration impedance (614) from the phase of the uncorrected object impedance (634), a calculating means (642) determines the magnitude of the object impedance from the ratio of the a priori known magnitude of the calibration impedance and the determined equivalent for the calibration impedance magnitude (612), multiplied by the determined equivalent for the object impedance magnitude (632), and wherein further in the event the real or imaginary portion of the object impedance is further processed, calculating means (644) for determining the in-phase portion (real part) and/or calculating means (646) for determining the quadrature portion (imaginary part) from the magnitude (642) and phase (640) of the object impedance.

(FIG. 6)

Entry 30. Apparatus according to any of entries 23 to 26, wherein:

for the demodulation when the switching means (30, 32, 34, 36; 700) connect the alternating current (AC) source (70, 40, 42) and the first measuring means (50, 52) to the object (10) in order to acquire Object Current Samples (702) and Object Voltage Samples (704), for each frequency $f_{AC}$ of the alternating current (AC) applied, a correlating means (706) correlates the Object Current Samples (702) with the discrete values of an ideal sine waveform in order to obtain a value (714) proportional to the in-phase portion of the alternating current (indirect correlation), a correlation means (708) correlates the Object Current Samples (702) with the discrete values of an ideal cosine waveform in order to obtain a value (716) proportional to the quadrature portion of the alternating current, a correlation means (710) correlates the Object Voltage Samples (704) with the discrete values of an ideal sine waveform to obtain a value (718) proportional to the in-phase portion of the voltage, a correlation means (712) correlates the Object Voltage Samples (704) with the discrete values of an ideal cosine waveform in order to obtain a value (720) proportional to the quadrature portion of the voltage, a calculation means (722) determines a current magnitude from the values proportional to in-phase portion (714) and quadrature portion (716) of the current applied, a calculation means (724) determines a voltage magnitude from the values proportional to in-phase portion (718) and quadrature portion (720) of the voltage measured, a calculation means (730) determines a current phase of the values proportional to in-phase portion (714) and quadrature portion (716) of the current applied, calculation means (732) determines a voltage phase from the values proportional to in-phase portion (718) and quadrature portion (720) of the voltage measured, a calculation means (734) determines the phase of the object impedance as the difference between the voltage phase (730) and the current phase (732), a calculation means (736) determines the magnitude of the object impedance from the ratio of voltage magnitude (724) and current magnitude (722), and wherein further in the event the real or imaginary portion of the object impedance is further processed, calculating means (738) for determining the in-phase portion (real part) of the object impedance and/or calculating means (740) for determining the quadrature portion of the object impedance from the magnitude (736) and phase (734) of the object impedance.

(FIG. 7)

Entry 31. Apparatus according to any of entries 23 to 26, comprising:

for the demodulation when the switching means (30, 32, 34, 36; 800) connect the alternating current (AC) source (40, 42) and the first measuring means (50, 52) to the object (10) in order to acquire Object Current Samples (802) and object Voltage Samples (804), a correlating means (806) for correlating the Object Current Samples (802) with the Object Voltage Samples (804) in order to obtain a value (810) proportional to the in-phase portion (real part) of the object impedance (direct correlation), a correlating means (808) for correlating the Object Current Samples (802) with the Object Voltage Samples (804), which are shifted in time by −90 degrees, in order to obtain a value (812) proportional to the quadrature portion (imaginary part) of the object impedance, and further comprising a calculating means (814) for determining the magnitude of the object impedance and/or a calculating means (816) for determining the phase of the object impedance, both from the in-phase portion (810) and quadrature portion (812) of the object impedance.

(FIG. 8)

Entry 32. Apparatus according to any of entries 23 to 26, wherein:

for the demodulation when the switching means (30, 32, 34, 36; 900) connect the alternating current (AC) source (70, 40, 42) of constant magnitude and the first measuring means (50, 52) to the object (10) in order to acquire Object Voltage Samples (902), for each frequency $f_{AC}$ of the alternating current (AC) applied, a sampling means for providing discrete values of an ideal sine waveform which represent the current in magnitude and phase, further referred to as the Reference Current Samples (REF), a correlation means (904) for correlating the Object Voltage Samples (902) with the Reference Current Samples (REF), to obtain a value (908) proportional to the in-phase portion (real part) of the object impedance, a correlation means (906) for correlating the Object Voltage Samples (902) with the Reference Current Samples (REF), to obtain a value (910) proportional to the quadrature portion (imaginary part) of the object impedance, and further comprising in the event the real or imaginary portion of the object impedance is further processed, a calculating means (912) for determining the magnitude of the object impedance and/or a calculating means (914) for determining the phase of the object impedance both from the in-phase portion (908) and quadrature portion (910) of the object impedance.

(FIG. 9)

Entry 33. Apparatus of any of entries 27 to 32, wherein fitting means are provided to fit the samples of the digitized current signals of the calibration impedance (20) and/or the object (10) towards discrete values of an ideal sinusoidal waveform, providing, over time, the Calibration and/or Object Current Samples (402, 452; 502, 522; 702, 802), and/or fitting means to fit the samples of the digitized voltage signals of the calibration impedance (20) and/or the object (10) towards values of an ideal sinusoidal waveform, providing, over time, the Calibration and/or Object Voltage Samples (404, 454; 504, 524; 602, 622; 704; 804, 902).

Entry 34. Apparatus of any of entries 27 to 32, wherein the complex bioadmittance is determined instead of the complex bioimpedance.

Some examples of the invention may be summarized as follows. A method and apparatus for digital demodulation by means of correlation and further processing of signals obtained in the single and multi-frequency measurement of electrical bioimpedance or bioadmittance in which the amplitude of changes or rate of changes thereof can be determined with a higher amplitude resolution than before. It comprises: signal generation means which apply an excitation signal and a first measuring means (44, 46; 50, 52) for acquiring, sampling and digitizing a response signal to said excitation signal with respect to frequency content, amplitude and phase, whereas said excitation signal is either held at a constant, known amplitude and defined by a digital excitation waveform or measured by a second measuring means for acquiring, sampling and digitizing said excitation signal; memory means (48, 58) for temporarily storing said digitized response signal and, optionally, said digitized excitation signal; digital demodulation means (80; 81-86) for correlating for each frequency of the excitation signal applied digitized samples of said digitized response signal with corresponding discrete values of a sinusoidal reference signal to the excitation signal or said excitation signal, respectively; processing means (60) for calculating for each frequency of the excitation signal applied complex values for the bioimpedance or bioadmittance from the output values of the digital demodulation means, a first separating means (64) for separation the base bioimpedance or bioadmittance from said waveforms; and either a second separating means (66) for separation the changes in the bioimpedance or bioadmittance from said waveforms, and a differentiating means (67) for obtaining the rate of change of said changes, or a differentiating means (67) means for obtaining the rate of change in the bioimpedance or bioadmittance waveforms; as well as recording means (110) for either recording the temporal course or recording the rate of change in said waveforms.

This invention is related to the field of digital demodulation and further processing of signals obtained from the measurement of electrical bioimpedance or bioadmittance in a biological object, for instance in a plant or a fruit thereof due to biological activity, or in an animal or a human due to cardiac and/or respiratory activity, for instance in cardiometry, in particular to the monitoring through measurement of the change in thoracic electrical bioimpedance (TEB) or bioadmittance, and pertains to the processing of the excitation, response and/or reference signals obtained through sensing and measuring excitation, response and/or reference signals, e.g., but not limited to, a voltage resulting from an alternating current (AC) application.

A number of illustrative embodiments of the invention have been described herein. It will be apparent to persons skilled in the art that various changes and modifications can be made to the described embodiments without departing from the scope of the invention as defined by the following claims.

What is claimed is:

1. A method for digital demodulation of signals obtained in the measurement of electrical bioimpedance of a human subject, wherein the method comprises the following operations:

applying the output of an AC current source to a calibration impedance, to cause an AC calibration current to flow through the calibration impedance;

producing a voltage that is directly proportional to, and in phase with, the output of the AC current source;

after producing the voltage, digitizing the voltage by a first analog-to-digital converter that is directly proportional to, and in phase with, the output of the AC current source, to produce Calibration Current Samples, a first sampling rate of the first analog-to-digital converter being significantly higher than a highest frequency of the output of the AC current source;

calculating a value proportional to an in-phase portion of the calibration current, by correlating the Calibration Current Samples with corresponding discrete values of a unity sine waveform;

calculating a value proportional to a quadrature portion of the calibration current, by correlating the Calibration Current Samples with corresponding discrete values of a unity cosine waveform;

calculating a magnitude of an equivalent to the current through the calibration impedance, by calculating the square root of the sum, of the squared in-phase portion of the calibration current and the squared quadrature portion of the calibration current;

calculating a phase of the calibration current including measurement system phase shift, by calculating the arctan of the ratio of the quadrature portion of the calibration current and the in-phase portion of the calibration current;

measuring a calibration voltage across the calibration impedance, wherein the measured voltage is produced due to application of the output of the AC current source to the calibration impedance;

after measuring the calibration voltage, digitizing the calibration voltage by a second analog-to-digital converter measured across the calibration impedance to produce Calibration Voltage Samples, a second sampling rate of the second analog-to-digital converter being significantly higher than the highest frequency of the output of the AC current source;

calculating a value proportional to an in-phase portion of the calibration voltage uncorrected for the measurement system phase shift, by correlating the Calibration Voltage Samples with corresponding discrete values of a unity sine waveform;

calculating a value proportional to a quadrature portion of the calibration voltage uncorrected for the measurement system phase shift, by correlating the Calibration Voltage Samples with corresponding discrete values of a unity cosine waveform;

calculating a magnitude of an equivalent to the voltage across the calibration impedance, by calculating the square root of the sum of the square of the value proportional to the in-phase portion of the calibration voltage and the square of the value proportional to the quadrature portion of the calibration voltage;

calculating a phase of the calibration voltage including the measurement system phase shift, by calculating the arctan of the ratio of the value proportional to the quadrature portion of the calibration voltage and the value proportional to the in-phase portion of the calibration voltage;

calculating an equivalent to the calibration impedance magnitude by calculating the ratio of the voltage magnitude equivalent across the calibration impedance and the magnitude of the current magnitude equivalent through the calibration impedance;

placing a first current electrode and a second current electrode in contact with the human subject;

placing a first voltage sensing electrode and a second voltage sensing electrode in contact with the human subject;

applying the output of the AC current source to the first current electrode and the second current electrode, to cause an AC human subject current to flow through the human subject between the first current electrode and the second current electrode;

producing a voltage that is directly proportional to, and in phase with, the output of the AC current source that is applied to the first current electrode and the second current electrode;

digitizing the voltage that is directly proportional to, and in phase with, the output of the AC current source, to produce Human Subject Current Samples;

calculating an in-phase portion of the AC current through the human subject uncorrected for the measurement system phase shift, by correlating the Human Subject Current Samples with corresponding discrete values of a unity sine waveform;

calculating a quadrature portion of the AC current through the human subject uncorrected for the measurement system phase shift, by correlating the Human Subject Current Samples with corresponding discrete values of a unity cosine waveform;

calculating an equivalent current magnitude through the human subject, by calculating the square root of the sum the squared in-phase portion of the current and the squared quadrature portion of the current through the human subject;

calculating a phase of the human subject current including the measurement system phase shift, by calculating the arctan of the ratio of the quadrature portion of the current and the in-phase portion of the current through the human subject;

measuring a human subject voltage between the first voltage sensing electrode and the second voltage sensing electrode, wherein the measured voltage is produced due to application of the output of the AC current source to the first current electrode and the second current electrode;

digitizing the voltage measured between the first voltage sensing electrode and the second voltage sensing electrode to produce Human Subject Voltage Samples;

calculating an in-phase portion of the human subject voltage uncorrected for the measurement system phase shift, by correlating the Human Subject Voltage Samples with corresponding discrete values of a unity sine waveform;

calculating a quadrature portion of the human subject voltage uncorrected for the measurement system phase shift, by correlating the Human Subject Voltage Samples with corresponding discrete values of a unity cosine waveform;

calculating an equivalent voltage magnitude across the human subject, by calculating the square root of the sum of the squared in-phase portion of the uncorrected human subject voltage and the squared quadrature portion of the uncorrected human subject voltage;

calculating a phase of the voltage across the human subject plus measurement system voltage phase shift, by calculating the arctan of the ratio of the quadrature portion of the human subject voltage and the in-phase portion of the human subject voltage;

calculating the magnitude equivalent of bioimpedance of the human subject, by calculating the ratio of the voltage equivalent magnitude across the human subject to the current magnitude equivalent through the human subject, multiplied by the cosine of the phase shift between the voltage across the human subject and the current through the human subject; and calculating the magnitude of the bioimpedance of the human subject by calculating the ratio of a previously known calibration impedance magnitude, to the magnitude equivalent of the calibration impedance, multiplied by the magnitude equivalent of the bioimpedance of the human subject.

2. The method of claim 1, wherein the operations further comprise:

providing, over time, a set of digital bioimpedance waveforms $Z(f_{AC},t)$);

separating a base bioimpedance $Z_0(f_{AC})$ from the waveforms;

separating changes of bioimpedance $\Delta Z(f_{AC},t)$ from the waveforms;

determining a rate of change of the bioimpedance $dZ(f_{AC},t)/dt$; and recording a temporal course of the base bioimpedance $Z_0(f_{AC})$ and of the rate of change of the bioimpedance $dZ(f_{AC},t)/dt$.

3. The method of claim 1:

wherein the AC human subject current has a plurality of frequencies; and wherein the measurement system phase shift is the difference between the phase of the calibration voltage and the phase of voltage corresponding to the output of an AC current source.

4. A method for digital demodulation of signals obtained in the measurement of electrical bioimpedance of a human subject, wherein the method comprises the following operations:

applying a calibration excitation signal to a calibration impedance;

measuring, sampling, and digitizing a signal representing the calibration excitation signal to acquire calibration Excitation Signal Samples, the digitizing of the calibration excitation signal being performed by a first analog-to-digital converter and a first sampling rate of the first analog-to-digital converter being significantly higher than a highest frequency of the calibration excitation signal;

for each frequency $f_{AC}$ of the calibration excitation signal applied to the calibration impedance, correlating the calibration Excitation Signal Samples with discrete values of an ideal sine waveform in order to obtain a value proportional to an in-phase portion of the calibration excitation signal related to the ideal sine waveform as a reference sine;

for each frequency $f_{AC}$ of the calibration excitation signal applied to the calibration impedance, correlating the calibration Excitation Signal Samples with discrete values of an ideal cosine waveform in order to obtain a value proportional to a quadrature portion of the calibration excitation signal;

measuring, sampling, and digitizing a calibration response signal across the calibration impedance to acquire calibration Response Signal Samples;

correlating the calibration Response Signal Samples with discrete values of an ideal sine waveform in order to obtain a value proportional to an in-phase portion of the calibration response signal;

correlating the calibration Response Signal Samples with discrete values of an ideal cosine waveform in order to obtain a value proportional to a quadrature portion of the calibration response signal;

calculating an equivalent for a magnitude and a phase of the calibration excitation signal;

calculating an equivalent for a magnitude and a phase of the calibration response signal;

calculating an equivalent for a magnitude of the calibration impedance;

calculating a system phase;

applying a human subject excitation signal to the human subject after the operation of calculating the system phase;

measuring, sampling, and digitizing a signal representing the human subject excitation signal to acquire human subject Excitation Signal Samples;

measuring, sampling and digitizing the human subject response signal across the bioimpedance of the human subject, the samples obtained from sampling the human subject response signal being called human subject Response Signal Samples, the digitizing of the human subject response signal being performed by a second analog-to-digital converter and a second sampling rate of the second analog-to-digital converter being significantly higher than a highest frequency of the human subject excitation signal;

for each frequency $f_{AC}$ of the human subject excitation signal applied, correlating the human subject Excitation Signal Samples with discrete values of an ideal sine waveform in order to obtain a value proportional to an in-phase portion of the human subject excitation signal related to the ideal sine waveform;

for each frequency $f_{AC}$ of the excitation signal applied, correlating the human subject Excitation Signal Samples with discrete values of an ideal cosine waveform in order to obtain a value proportional to a quadrature portion of the human subject excitation signal;

correlating the human subject Response Signal Samples with discrete values of another ideal sine waveform in order to obtain a value proportional to an in-phase portion of the human subject response signal;

correlating the human subject Response Signal Samples with discrete values of another ideal cosine waveform in order to obtain a value proportional to a quadrature portion of the human subject response signal;

calculating an equivalent for the magnitude and a phase of the human subject excitation signal;

calculating an equivalent for the magnitude and a phase of the human subject response signal;

calculating an equivalent for the magnitude and a phase of the bioimpedance of the human subject;

calculating a magnitude of the bioimpedance $Z(f_{AC},t)$ of the human subject by calculating the ratio of a previously known calibration impedance magnitude, to the magnitude equivalent of the calibration impedance, multiplied by the magnitude equivalent of the bioimpedance of the human subject; and calculating an in-phase portion $Re(Z(f_{AC},t))$ and a quadrature portion $Im(Z(f_{AC},t))$ of the bioimpedance of the human subject.

5. The method of claim 4, further comprising calculating a cross-correlation signal, wherein the cross-correlation signal is a function of a time delay $\tau$ between the human subject excitation signal and the human subject response signal, wherein the cross-correlation signal is calculated by correlating the human subject excitation signal with the human subject response signal after delay of the human subject response signal by the time delay $\tau$ with respect to the human subject excitation signal.

6. The method of claim 4, further comprising calculating a complex Fourier transform of the cross-correlation signal, to obtain complex values proportional to a complex bioimpedance.

* * * * *